(12) United States Patent
Narizuka et al.

(10) Patent No.: US 8,003,749 B2
(45) Date of Patent: Aug. 23, 2011

(54) FLUORINE-CONTAINING DICARBOXYLIC ACIDS AND THEIR NOVEL POLYMER COMPOUNDS

(75) Inventors: Satoru Narizuka, Saitama (JP); Yuji Hagiwara, Kawagoe (JP); Masashi Nagamori, Fujimino (JP); Kazuhiro Yamanaka, Kokubunji (JP)

(73) Assignee: Central Glass Company, Limited, Ube-shi (JP)

( * ) Notice: Subject to any disclaimer, the term of this patent is extended or adjusted under 35 U.S.C. 154(b) by 500 days.

(21) Appl. No.: 12/174,414

(22) Filed: Jul. 16, 2008

(65) Prior Publication Data
US 2009/0030173 A1 Jan. 29, 2009

(30) Foreign Application Priority Data
Jul. 17, 2007 (JP) ................... 2007-185257

(51) Int. Cl.
*C08G 75/00* (2006.01)
(52) U.S. Cl. ........ 528/173; 528/176; 528/169; 528/361; 528/347; 528/348
(58) Field of Classification Search .......... 528/173, 528/176, 169, 361, 347, 348
See application file for complete search history.

(56) References Cited

U.S. PATENT DOCUMENTS
4,045,408 A * 8/1977 Griffith et al. ............ 528/102

FOREIGN PATENT DOCUMENTS

| | | | |
|---|---|---|---|
| CA | 2 614 648 A1 | 1/2007 | |
| EP | 1 783 158 A1 | 5/2007 | |
| EP | 1 810 963 A1 | 7/2007 | |
| EP | 1 832 618 A1 | 9/2007 | |
| JP | 2003-206352 A | 7/2003 | |
| JP | 2003-268233 A | 9/2003 | |
| JP | 2007-119503 A | 5/2007 | |
| JP | 2007-119504 A | 5/2007 | |
| WO | WO 2006/070728 A1 | 7/2006 | |
| WO | WO 2007/010932 A1 | 1/2007 | |

OTHER PUBLICATIONS

USPTO search report, Apr. 2011.*
H. Ito et al., "Fluoropolymer Resists: Fundamentals and Lithographic Evaluation", Journal of Photopolymer Science and Technology, 2004, pp. 609-619, vol. 17, No. 4.
U.S. Appl. No. 10/586,184, "Fluorine-Containing Polymerizable Monomer and Polymer Compound Using Same", Jul. 14, 2006.
U.S. Appl. No. 10/586,183, "Fluorine-Containing Polymerizable Monomer and Polymer Compound Using Same", Jul. 14, 2006.

* cited by examiner

*Primary Examiner* — James Seidleck
*Assistant Examiner* — Gregory Listvoyb
(74) *Attorney, Agent, or Firm* — Crowell & Moring LLP

(57) ABSTRACT

Disclosed is a fluorine-containing dicarboxylic acid represented by formula (1),

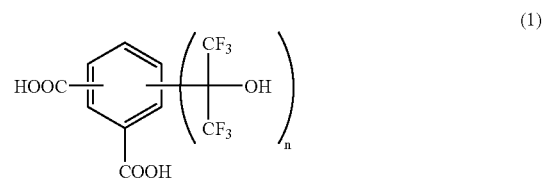

(1)

wherein n represents an integer of 1-4, and the two carboxylic groups are not adjacent to each other on the aromatic ring. It is possible to obtain a linear polymer compound by reacting the fluorine-containing dicarboxylic acid with a comonomer (e.g., diaminodiol). By thermal cyclization, this linear polymer compound can be converted into another polymer compound having superior characteristics.

8 Claims, No Drawings

FLUORINE-CONTAINING DICARBOXYLIC ACIDS AND THEIR NOVEL POLYMER COMPOUNDS

BACKGROUND OF THE INVENTION

The present invention relates to novel fluorine-containing dicarboxylic acids and novel polymer compounds derived from the same.

Polyester, polyamide, polyimide, and polybenzoxazole have been developed as representatives of organic polymers having high heat resistance. They form a large market in electronic device field, engineering plastic field for automobile and aerospace uses, etc., fuel cell field, medical material field, optical material field, etc. As their center, various many polymers have been put into practical uses, such as polyamides represented by nylon and Kevlar, polyacrylates used for liquid crystal polymers, polyimides represented by Kapton, and polybenzoxazoles represented by Zylon.

It is possible to produce polyester by a process by a polycondensation between dicarboxylic acid and diol in the presence of a condensing agent or by a process by converting dicarboxylic acid into an acid chloride or ester, followed by a polycondensation with diol. It is possible to produce polyamide by a process by a polycondensation between dicarboxylic acid and diamine in the presence of a condensing agent or by a process by converting dicarboxylic acid into a carboxylic chloride or ester, followed by a polycondensation with diamine. It is possible to produce polyimide by polymerizing diamine with tetracarboxylic dianhydride, followed by a dehydration, ring-closing reaction. It is possible to produce polybenzoxazole by a process by a polycondensation between dicarboxylic acid and bisaminophenol in the presence of a condensing agent and then a dehydration, ring-closing reaction. Alternatively, it may be conducted by converting dicarboxylic acid into a carboxylic chloride or ester, then a polycondensation with bisaminophenol, and then a dehydration, ring-closing reaction.

In research and development of these resins, it has widely been tried to introduce a hydroxy group(s), which is not directly involved in the polymerization (polycondensation) and remains in the resin even after the polycondensation, into the monomer to provide the resin with a further function(s). For example, in Japanese Patent Application Publication 2003-268233 A (Patent Publication 1), a phenolic hydroxy group is introduced as a photosensitive group for providing the resin with alkali solubility. In Japanese Patent Application Publication 2003-206352 A (Patent Publication 2), a phenolic hydroxy group is introduced as an adhesive group for providing adhesion between fibers and a resin matrix in a composite material. In International Publication WO 2007/010932 A1 or its corresponding Canadian Patent Application Publication 2614648 A1 (Patent Publication 3), a phenolic hydroxy group is introduced as a crosslinking point moiety.

The resin of Patent Publication 1 is described therein as a polybenzoxazole. To produce this polybenzoxazole, there is conducted a polycondensation between a bisaminophenol derivative (a polymerizable monomer), in which an amino group and a phenolic hydroxy group are adjacent to each other, and a dicarboxylic acid, thereby firstly synthesizing a polyamidephenol precursor containing phenolic hydroxy groups. The phenolic hydroxy group of this precursor serves as a photosensitive group upon patterning by photolithography and then disappears by the subsequent heating as the precursor is modified into an oxazole ring of the final product.

In contrast, In Patent Publications 2 or 3, hydroxyl group is used mainly as an adhesive group or crosslinking point moiety and partly remains in the final product.

Recently, there have been active research and development in the fields of photoresist material and the like by using fluorine-containing compounds, which are superior in transparency in ultraviolet region, particularly in vacuum ultraviolet region. In particular, fluorine-containing hydroxy compounds (fluorocarbinols) are often used. Fluorine is introduced as fluorocarbinol group to achieve adhesion to substrate, high glass transition point, photosensitivity, while allowing transparency at each wavelength for use, due to acidity of fluorocarbinol group, alkali development property, and the like. Of fluorocarbinol group, particularly hexafluoroisopropanol moiety (i.e., 2,2,2-trifluoro-1-hydroxy-1-(trifluoromethyl)ethyl group) attracts much attention due to its dissolution behavior, anti-swelling property, and high contrast, etc. Therefore, a lot of research and development is conducted (see Journal of Photopolymer Science and Technology, Volume 17, No. 14 (2004) pp. 609-619 (Non-patent Publication 1) and International Publication WO 2006/070728 A1 or its corresponding European Patent Application Publication EP 1832618 A1 (Patent Publication 4)).

Fluorine-containing compounds are under development and practical use in the field of various materials, such as polyolefins and condensed polymers, mainly in the field of advanced materials, due to characteristics of fluorine, such as water repellency, oil repellency, low water absorption, heat resistance, weather resistance, corrosion resistance, transparency, photosensitivity, low refractive index, and low-dielectric constant. In the field of condensed polymers, there are proposals for introducing fluorine into diamine monomers, such as a diamine monomer containing a fluorine atom(s) or trifluoromethyl group(s) substituted for a hydrogen(s) of its benzene ring, a diamine monomer containing a hexafluoroisopropenyl group introduced between two aromatic rings, and a fluorine-containing diamine monomer in which a benzene ring has been subjected to hydrogen reduction. Furthermore, a bishydroxyamine monomer containing a hexafluoroisopropenyl group as a center atomic group and aromatic hydroxyamines at its both sides is in practical use. In this case, it is applied as polybenzoxazole or hydroxy-containing polyimide.

There are, however, few developments of heat resistant polymers (e.g., polyester, polyamide, polyimide, and polybenzoxazole) containing a hexafluoroisopropanol moiety as acidic alcohol (see Patent Publication 4, Japanese Patent Application Publication 2007-119503 or its corresponding European Patent Application Publication EP 1783158 A1 (Patent Publication 5), Japanese Patent Application Publication 2007-119504 or its corresponding European Patent Application Publication EP 1810963 A1 (Patent Publication 6), and U.S. Pat. No. 4,045,408 (Patent Publication 7)).

SUMMARY OF THE INVENTION

The polybenzoxazole resin of Patent Publication 1 has an advantageous effect of lowering swelling in developing solution, as compared with conventional polyimide resins using a carboxyl group in polyamide acid as a developing solution-soluble group. However, as mentioned above, since there is no phenolic hydroxy group remaining in the final product, it is difficult to make the hydroxy group to contribute to adhesion to substrate or the like.

In the cases of Patent Publications 2 and 3, a phenolic hydroxy group remains in the final product. Therefore, it is possible to improve adhesion to substrate and the like and to use the phenolic hydroxy group in a cross-linking reaction with epoxy resin. On the other hand, the phenolic hydroxy group remaining in the final product becomes a cause for increasing hygroscopic property. Therefore, in the case of using it for electronic material components such as LSI, it may cause the increase of dielectric constant, cracks and the like.

Under such background, Patent Publication 4 proposes the introduction of a hexafluoroisopropanol moiety (i.e., 2,2,2-trifluoro-1-hydroxy-1-(trifluoromethyl)ethyl group) in place of phenolic hydroxy group. In fact, this publication discloses a synthesis of polyamide or polyimide from a diamine containing hexafluoroisopropanol moiety and a dicarboxylic acid or tetracarboxylic dianhydride. It is mentioned that these polyamide and polyimide show lower dielectric constant and lower water absorption, as compared with conventional polymers derived from a diamine containing a phenolic hydroxy group(s).

The polymer of Patent Publication 4 is, however, characterized in that an aromatic ring is bonded as a side chain to the main chain of the polymer through an ester bond and that this aromatic ring has a hexafluoroisopropanol moiety as a substituent. Although this polymer has superior characteristics, a relatively bulky side chain is bonded to the main chain through a hydrolysable ester bond, and acidic OH groups are positioned at a terminal portion of the side chain. Therefore, environment for its use is somewhat limited to sufficiently show its capacities.

Furthermore, the synthesis of a diamine containing a hexafluoroisopropanol moiety as a constituent component of the polymer of Patent Publication 4 requires a relatively high cost. In the case of a diamine containing a hexafluoroisopropanol moiety, the resin is limited to a resin (e.g., polyamide, polyimide and polybenzoxazole) prepared by the formation of amide bond as a polymerization elementary reaction, and it cannot be used for synthesizing ester-series resins.

The polymers of Patent Publications 5 and 6 have a polyamide basic skeleton containing a hexafluoroisopropanol moiety as an acidic alcohol, and achieve high transparency, low dielectric constant, low water absorption, heat resistance, weather resistance, corrosion resistance, photosensitivity, and low refractive index, which are derived from fluorine, while maintaining capabilities as heat resistant polymers. In a final dehydration, ring-closing reaction (a thermal cyclization between a OH group and an amide bond moiety) of the polymers, however, the OH group disappears by incorporation into the resin skeleton. Therefore, it is difficult in the final polymers after the thermal cyclization to sufficiently maintain adhesion and compatibility with other resins, which are derived from OH group.

Furthermore, imine by-products are produced in the productions of diamine monomers of Patent Publications 5 and 6, and there occurs a load of separating the imine by-product from the target polymer.

As an example that a hexafluoroisopropanol moiety has been introduced into a dicarboxylic acid monomer, Patent Publication 7 discloses a phthalic derivative, which is defined as a dicarboxylic acid derivative containing two carboxyl groups at ortho position of the benzene nucleus. In this publication, an anhydride of a phthalic acid derivative containing a hexafluoroisopropanol moiety is used as a curing agent for epoxy resins. It is possible to convert this phthalic acid derivative to other compounds by using reactivity of its anhydride. This phthalic acid derivative is, however, not suitable for synthesizing linear polymers such as polyester, polyamide and polybenzoxazole.

As mentioned above, there has been a demand for a linear polymer, such as polyester, polyamide and polybenzoxazole, particularly a novel aromatic polymer oriented to heat resistance, which has a repeating unit derived from a dicarboxylic acid monomer having a hexafluoroisopropanol moiety.

As a result of an eager examination to meet the above-mentioned demand, the present inventors have reached a novel dicarboxylic acid containing at least one hexafluoroisopropanol moiety in the molecule and novel polymer compounds obtained by using the same.

That is, we have found a fluorine-containing dicarboxylic acid represented by formula (1),

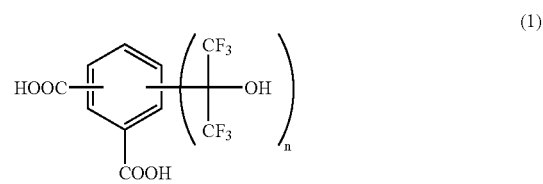

wherein n represents an integer of 1-4, and the two carboxylic groups are not adjacent to each other on the aromatic ring.

We have found that the fluorine-containing dicarboxylic acid has properties that are significantly different from those of the above-mentioned phthalic acid derivative (i.e., a dicarboxylic acid derivative containing two carboxyl groups adjacent to each other on the aromatic ring) of Patent Publication 7. In fact, we have found that the fluorine-containing dicarboxylic acid can perform effectively as a unit for synthesizing various linear polymers, such as polyester, polyamide and polybenzoxazole.

That is, firstly, we have found a first polymer compound obtained by reacting the fluorine-containing dicarboxylic acid or an ester-forming derivative thereof with a diol represented by formula (2),

HO—R$^1$—OH    (2)

wherein R$^1$ represents an organic group that has a valence of at least two and that contains at least one selected from the group consisting of aliphatic rings, aromatic rings, condensed polycyclic aromatic rings, and heterocycles, R$^1$ may contain fluorine, chlorine, oxygen, sulfur or nitrogen, a part of hydrogen atoms of R$^1$ may be replaced with an alkyl group, fluoroalkyl group, carboxyl group, hydroxy group, or cyano group.

The first polymer compound is represented by formula (6),

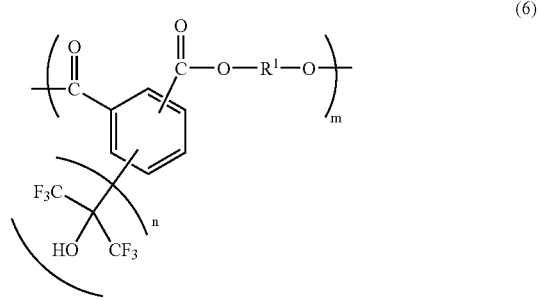

wherein n and $R^1$ are respectively defined as in formulas (1) and (2), the two —CO groups are not adjacent to each other on the aromatic ring, and m represents a positive integer.

Secondly, we have found a second polymer compound obtained by reacting the fluorine-containing dicarboxylic acid or an amide-forming derivative thereof with a diamine represented by formula (3),

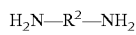  (3)

wherein $R^2$ represents an organic group that has a valence of at least two and that contains at least one selected from the group consisting of aliphatic rings, aromatic rings, condensed polycyclic aromatic rings, and heterocycles, $R^2$ may contain fluorine, chlorine, oxygen, sulfur or nitrogen, a part of hydrogen atoms of $R^2$ may be replaced with an alkyl group, fluoroalkyl group, carboxyl group, hydroxy group, or cyano group.

The second polymer compound is represented by formula (7),

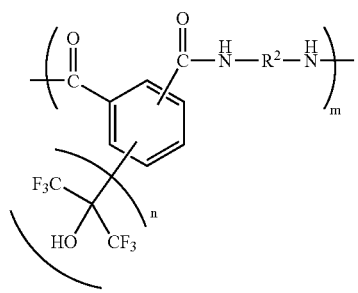

wherein n and $R^2$ are respectively defined as in formulas (1) and (3), the two —CO groups are not adjacent to each other on the aromatic ring, and m represents a positive integer.

Thirdly, we have found a third polymer compound obtained by reacting the fluorine-containing dicarboxylic acid or an amide-forming derivative thereof with a diaminodiol represented by formula (4),

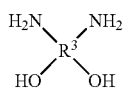  (4)

wherein $R^3$ represents an organic group that has a valence of at least four and that contains at least one selected from the group consisting of aliphatic rings, aromatic rings, condensed polycyclic aromatic rings, and heterocycles, $R^3$ may contain fluorine, chlorine, oxygen, sulfur or nitrogen, a part of hydrogen atoms of $R^3$ may be replaced with an alkyl group, fluoroalkyl group, carboxyl group, hydroxy group, or cyano group.

The third polymer compound is represented by formula (8),

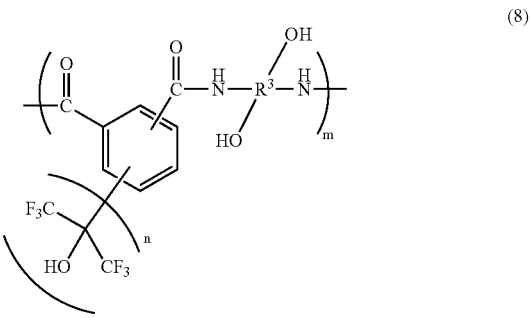

wherein n and $R^3$ are respectively defined as in formulas (1) and (4), the two —CO groups are not adjacent to each other on the aromatic ring, and m represents a positive integer.

Fourthly, we have found a fourth polymer compound obtained by reacting the fluorine-containing dicarboxylic or an amide-forming derivative thereof with a diaminodiol represented by formula (5),

wherein $R^4$ represents an organic group that has a valence of at least four and that contains at least one selected from the group consisting of aliphatic rings, aromatic rings, condensed polycyclic aromatic rings, and heterocycles, $R^4$ may contain fluorine, chlorine, oxygen, sulfur or nitrogen, a part of hydrogen atoms of $R^4$ may be replaced with an alkyl group, fluoroalkyl group, carboxyl group, hydroxy group, or cyano group.

The fourth polymer compound is represented by formula (10),

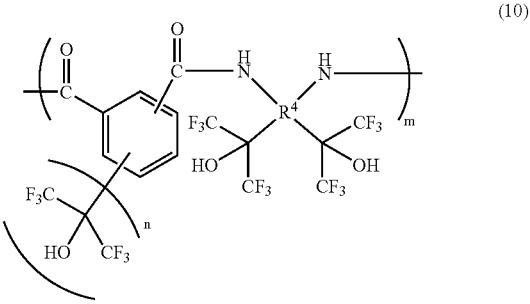

wherein n and $R^4$ are respectively defined as in formulas (1) and (5), the two —CO groups are not adjacent to each other on the aromatic ring, and m represents a positive integer.

Furthermore, we have found a fifth polymer compound obtained by a dehydration, ring-closing reaction of the third polymer compound represented by formula (8). The fifth polymer compound is represented by formula (9),

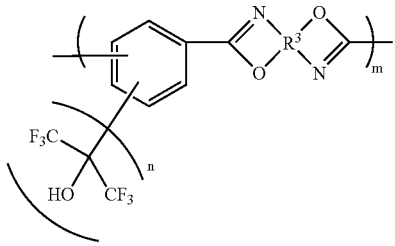

(9)

wherein n, $R^3$ and m are respectively defined as in formulas (1), (4) and (8), and a main chain of the polymer compound is not bonded to adjacent positions on the aromatic ring.

Furthermore, we have found a sixth polymer compound obtained by a dehydration, ring-closing reaction of the fourth polymer compound represented by formula (10). The sixth polymer compound is represented by formula (11),

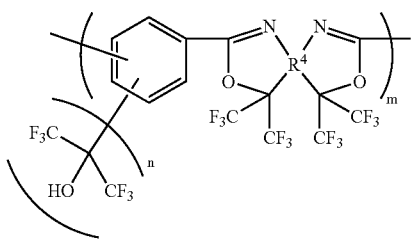

(11)

wherein n, $R^4$ and m are respectively defined as in formulas (1), (5) and (10), and a main chain of the polymer compound is not bonded to adjacent positions on the aromatic ring.

The first to sixth polymer compounds according to the present invention are resins characterized in that fluorine is contained and that a free acidic OH group(s) exists in the vicinity of the polymer main chain. Due to the existence of this acidic OH group, the resins show superior photosensitivity, adhesion, compatibility with other resins (for example, showing of a prompt and uniform alkali solubility), or reactivity (for example, reactivity for serving as cross-linking points).

It is a great advantage that the OH group introduction does almost not damage the first to sixth polymer compounds with respect to characteristics derived from fluorine atom, such as low water absorption, low dielectric constant, high weather resistance, high corrosion resistance, transparency and low refractive index. This is supported by the fact that the polymer compounds of the present invention show clearly superior values in water absorption characteristics and dielectric constant, as compared with their corresponding polymer compounds each containing a phenolic hydroxy group (see the after-mentioned Examples and Comparative Examples).

Of the above first to sixth polymer compounds, the fifth and sixth polymer compounds each obtained by the above dehydration, ring-closing reaction are useful substances, since they are particularly high in heat resistance.

That is, we have succeeded in finding novel polymer compounds each having (a) a heat resistance derived from a basic skeleton of the polymer, (b) characteristics derived from fluorine atom, such as low water absorption, low dielectric constant, high weather resistance, high corrosion resistance, transparency, and low refractive index, (c) characteristics derived from acidic OH group, such as photosensitivity, adhesion, compatibility, and reactivity, and a good balance of these (a), (b) and (c).

The fluorine-containing dicarboxylic acid represented by formula (1) of the present invention contains at least one hexafluoroisopropanol moiety introduced into dicarboxylic acid. With this, it became possible to avoid the above-mentioned problem of imine by-product production upon introducing a hexafluoroisopropanol moiety into diamine monomers in Patent Publications 5 and 6.

Furthermore, we have found a simple process for producing 5-[2,2,2-trifluoro-1-hydroxy-1-(trifluoromethyl)ethyl]-1,3-benzenedicarboxylic acid, which corresponds to the fluorine-containing dicarboxylic acid represented by formula (1). This process (first process) includes the step of carbonylating 5-[2,2,2-trifluoro-1-hydroxy-1-(trifluoromethyl)ethyl]-1,3-dihalobenzene represented by formula (12),

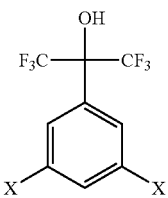

(12)

wherein X represents a halogen that is fluorine, chlorine, bromine or iodine, trifluoromethanesulfonate group, $C_1$-$C_4$ alkylsulfonate group, or arylsulfonate group.

The starting material of the first process, 5-[2,2,2-trifluoro-1-hydroxy-1-(trifluoromethyl)ethyl]-1,3-dihalobenzene, can be produced by a second process including the steps of:

(a) reacting a 1,3,5-trihalobenzene represented by formula (13),

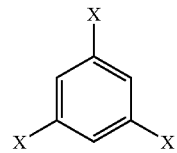

(13)

wherein X represents a halogen that is fluorine, chlorine, bromine or iodine, trifluoromethanesulfonate group, $C_1$-$C_4$ alkylsulfonate group, or arylsulfonate group, with an alkylmagnesium halide, metallic magnesium or alkyllithium; and (b) treating a product of the step (a) with hexafluoroacetone.

DETAILED DESCRIPTION

In the following, the present invention is exemplarily described in detail by certain embodiments. A person skilled in the art may modify the embodiments without deviating from the gist of the present invention. It should be understood that such modification is in the scope of the present invention.

Novel Fluorine-Containing Dicarboxylic Acid

As stated above, a novel fluorine-containing dicarboxylic acid according to the present invention is represented by formula (1),

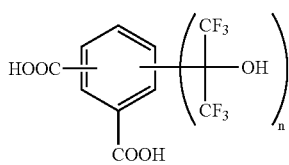

(1)

wherein n represents an integer of 1-4, and the two carboxylic groups are not adjacent to each other on the aromatic ring.

Specific examples of the fluorine-containing dicarboxylic acid include
2-[2,2,2-trifluoro-1-hydroxy-1-(trifluoromethyl)ethyl]-1,3-benzenedicarboxylic acid,
4-[2,2,2-trifluoro-1-hydroxy-1-(trifluoromethyl)ethyl]-1,3-benzenedicarboxylic acid,
5-[2,2,2-trifluoro-1-hydroxy-1-(trifluoromethyl)ethyl]-1,3-benzenedicarboxylic acid,
2,4-bis[2,2,2-trifluoro-1-hydroxy-1-(trifluoromethyl)ethyl]-1,3-benzenedicarboxylic acid,
2,5-bis[2,2,2-trifluoro-1-hydroxy-1-(trifluoromethyl)ethyl]-1,3-benzenedicarboxylic acid,
4,5-bis[2,2,2-trifluoro-1-hydroxy-1-(trifluoromethyl)ethyl]-1,3-benzenedicarboxylic acid,
4,6-bis[2,2,2-trifluoro-1-hydroxy-1-(trifluoromethyl)ethyl]-1,3-benzenedicarboxylic acid,
2,4,5-tris[2,2,2-trifluoro-1-hydroxy-1-(trifluoromethyl)ethyl]-1,3-benzenedicarboxylic acid,
2,4,6-tris[2,2,2-trifluoro-1-hydroxy-1-(trifluoromethyl)ethyl]-1,3-benzenedicarboxylic acid,
4,5,6-tris[2,2,2-trifluoro-1-hydroxy-1-(trifluoromethyl)ethyl]-1,3-benzenedicarboxylic acid,
2,4,5,6-tetrakis[2,2,2-trifluoro-1-hydroxy-1-(trifluoromethyl)ethyl]-1,3-benzenedicarboxylic acid,
2-[2,2,2-trifluoro-1-hydroxy-1-(trifluoromethyl)ethyl]-1,4-benzenedicarboxylic acid,
3-[2,2,2-trifluoro-1-hydroxy-1-(trifluoromethyl)ethyl]-1,4-benzenedicarboxylic acid,
2,3-bis[2,2,2-trifluoro-1-hydroxy-1-(trifluoromethyl)ethyl]-1,4-benzenedicarboxylic acid,
2,5-bis[2,2,2-trifluoro-1-hydroxy-1-(trifluoromethyl)ethyl]-1,4-benzenedicarboxylic acid,
2,6-bis[2,2,2-trifluoro-1-hydroxy-1-(trifluoromethyl)ethyl]-1,4-benzenedicarboxylic acid,
2,3,5-tris[2,2,2-trifluoro-1-hydroxy-1-(trifluoromethyl)ethyl]-1,4-benzenedicarboxylic acid, and
2,3,5,6-tetrakis[2,2,2-trifluoro-1-hydroxy-1-(trifluoromethyl)ethyl]-1,4-benzenedicarboxylic acid.

The fluorine-containing dicarboxylic acid represented by formula (1) is preferably one wherein n is 1 or 2 due to its availability, particularly preferably one wherein n is 1 due to its easy production.

It is an important point of the present invention that a phthalic acid derivative (i.e., a dicarboxylic acid derivative in which two carboxylic groups are adjacent to each other on the aromatic ring) is excluded from the fluorine-containing dicarboxylic acid of the present invention. In other words, the fluorine-containing dicarboxylic acid represented by formula (1) is a compound in which two carboxylic groups are at meta or para position. This position of the two carboxylic groups unexpectedly provides the fluorine-containing dicarboxylic acid with good polymerizability.

The process for synthesizing the fluorine-containing dicarboxylic acid can be based on Journal of Organic Chemistry, 1965, Volume 30, pp. 998-1001 and U.S. Pat. No. 4,045,408. That is, as shown in the following reaction formula [1], a xylene (o-xylene, m-xylene or p-xylene) is reacted with hexafluoroacetone to introduce one to four 2,2,2-trifluoro-1-hydroxy-1-(trifluoromethyl)ethyl groups. Then, the methyl groups are oxidized by using an oxidizer (e.g., potassium permanganate) to obtain the target dicarboxylic acid.

Reaction Formula (1)

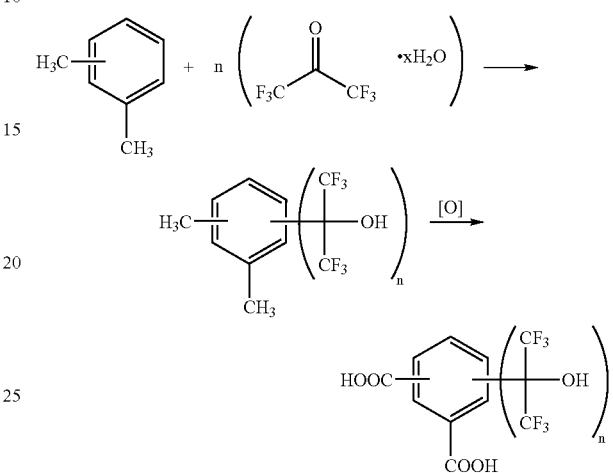

wherein n represents an integer of 1-4, and x represents an arbitrary number of 0-3.

By using the above process, it is possible to produce 2-[2,2,2-trifluoro-1-hydroxy-1-(trifluoromethyl)ethyl]-1,4-benzenedicarboxylic acid and 4-[2,2,2-trifluoro-1-hydroxy-1-(trifluoromethyl)ethyl]-1,3-benzenedicarboxylic acid, which are novel dicarboxylic acids (see Examples 1 and 2).

Novel Polymer Compounds Obtained by Using Novel Fluorine-Containing Dicarboxylic acid As a use of the fluorine-containing dicarboxylic acid according to the present invention, it can be polymerized to produce polymer compounds. Since this fluorine-containing dicarboxylic acid represented by formula (1) has at least one hexafluoroisopropanol moiety (2,2,2-trifluoro-1-hydroxy-1-(trifluoromethyl)ethyl group), it has at least three functional groups at the same time in the molecule. These at least three functional groups can effectively be used for producing polymer compounds. Specifically, it is preferable to use reactivity of dicarboxylic groups.

In formulas (6) to (11) of the polymer compounds of the present invention, m (a positive integer) means the number of the repetitions of the monomer unit in the polymer compound. It is preferably 5-10,000, more preferably 10-1,000. The polymer compound of the present invention refers to a mixture of polymer compounds having a certain range of the degree of polymerization. It is preferably 1,000-5,000,000, particularly preferably 2,000-200,000, in weight average molecular weight. It is possible to set the degree of polymerization and molecular weight of the polymer compound at desired values by suitably adjusting the after-mentioned polymerization conditions.

Polyester Type Polymer Compound

It is possible to conduct a polymerization by bringing the dicarboxylic acid (a fluorine-containing polymerizable monomer) represented by formula (1) into contact with a diol represented by formula (2),

HO—R¹—OH                    (2)

in a given range of temperature, thereby obtaining a polyester type polymer compound represented by formula (6).

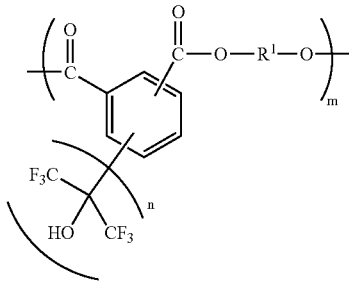

(6)

Specific examples of the diol represented by formula (2) include catechol (1,2-benzenediol), 1,3-benzenediol, 2,2'-dihydroxybiphenyl, 4,4'-dihydroxybiphenyl, 2,2'-methylenediphenol, 4,4'-methylenediphenol, ethylene glycol, propylene glycol, 2,2-bis(4-hydroxyphenyl)propane, 2,2-bis(4-hydroxyphenyl)-3-methylpropane, 2,2-bis(4-hydroxyphenyl)butane, 3,3-bis(4-hydroxyphenyl)pentane, 2,2-bis(4-hydroxyphenyl)-4-methylpentane, 3,3-bis(4-hydroxyphenyl)hexane, 2,2-bis(3-chloro-4-hydroxyphenyl)propane, 2,2-bis(3,5-dichloro-4-hydroxyphenyl)propane, 2,2-bis(3-bromo-4-hydroxyphenyl)propane, 2,2-bis(3,5-dibromo-4-hydroxyphenyl)propane, 2,2-bis(3-methyl-4-hydroxyphenyl)propane, and 2,2-bis(4-hydroxyphenyl)-1,1,1,3,3,3-hexafluoropropane.

The polyester type polymer compound can be produced by using a conventional polyester production process without particular limitation. For example, the polymer compound represented by formula (6) can be produced by a direct polycondensation (dehydrocondensation) between the fluorine-containing dicarboxylic acid represented by formula (1) and the diol represented by formula (2) in the presence of a condensing agent. Furthermore, it is also possible to use an ester-forming derivative of the fluorine-containing dicarboxylic acid. Herein, "ester-forming derivative" refers to a compound that easily forms an ester bond with a chemical reaction. In fact, the fluorine-containing dicarboxylic acid can be converted into an ester-forming derivative, such as acid halide (e.g., dichloride and dibromide of the dicarboxylic acid), dialkylester (e.g., dimethyl ester and diethyl ester of the dicarboxylic acid), ester having an active ester group (e.g., phenylester group, pyridylester group, succinimide ester group), and mixed acid anhydride. Then, it is possible to produce the polymer compound represented by formula (6) by reacting such ester-forming derivative with the diol represented by formula (2). In this case, it is also possible to use a polymer dissolution accelerator (i.e., a metal salt such as lithium bromide and lithium chloride) and a dehydrating agent such as sulfuric acid.

The process and the conditions of polymerization (polycondensation) are not particularly limited. For example, it is possible to use a first process in which an ester-forming derivative of the fluorine-containing dicarboxylic acid and the diol are dissolved or melted with each other at a temperature of 150° C. or higher to conduct the reaction without solvent. It is possible to use a second process in which the reaction is conducted in organic solvent at a high temperature (preferably 150° C. or higher). It is possible to use a third process in which the reaction is conducted in organic solvent at a temperature of −20 to 80° C.

It is simplest to use a process by mixing an ester-forming derivative of the fluorine-containing dicarboxylic acid represented by formula (1) with the diol represented by formula (2) in organic solvent to conduct the polycondensation. The molar ratio of this ester-forming derivative to the diol may be 0.5 to 1.5, preferably 0.8 to 1.2. Similar to normal polycondensation reactions, molecular weight of the obtained polymer becomes larger as this molar ratio gets closer to 1.

The organic solvent usable in the polycondensation is not particularly limited, as long as it can dissolve the both reactants. Its examples include amide solvents (e.g., N,N-dimethylformamide, N,N-dimethylacetamide, N-methylformamide, hexamethylphosphoric triamide, and N-methyl-2-pyrrolydone), aromatic solvents (e.g., benzene, anisole, diphenyl ether, nitrobenzene, and benzonitrile), halogen-containing solvents (e.g., chloroform, dichloromethane, 1,2-dichloroethane, and 1,1,2,2-tetrachloroethane), and lactones (e.g., γ-butyrolactone, γ-valerolactone, δ-valerolactone, γ-caprolactone, ∈-caprolactone, and α-methyl-γ-butyrolactone. It is effective to conduct the reaction under coexistence of an acid acceptor (e.g., pyridine and triethylamine) with such organic solvent. In particular, if the above amide solvent is used, the solvent itself becomes an acid acceptor. With this, it is possible to obtain a polyester resin that is high in degree of polymerization.

Polyamide Type Polymer Compound

It is possible to conduct a polymerization by bringing the dicarboxylic acid (a fluorine-containing polymerizable monomer) represented by formula (1) into contact with a diamine represented by formula (3),

(3)

in a given range of temperature, thereby obtaining a polyamide type polymer compound represented by formula (7).

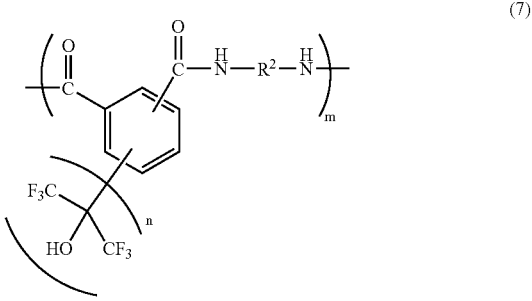

(7)

Specific preferable examples of the diamine represented by formula (3) include 3,5-diaminobenzotrifluoride, 2,5-diaminobenzotrifluoride, 3,3'-bis(trifluoromethyl)-4,4'-diaminobiphenyl, 3,3'-bis(trifluoromethyl)-5,5'-diaminobiphenyl, bis(trifluoromethyl)-4,4'-diaminodiphenyl, bis(fluorinated alkyl)-4,4'-diaminodiphenyls, dichloro-4,4'-diaminodiphenyl, dibromo-4,4'-diminodiphenyl, bis(fluorinated alkoxy)-4,4'-diaminodiphenyls, diphenyl-4,4'-diaminodiphenyl, 4,4'-bis(4-aminotetrafluorophenoxy)tetrafluorobenzene, 4,4'-bis(4-aminotetrafluorophenoxy)octafluorobiphenyl, 4,4'-binaphthylamine, o-, m- or p-phenylenediamine, 2,4-diaminotoluene, 2,5-diaminotoluene, 2,4-diaminoxylene, 2,4-diaminodurene, dimethyl-4,4'-diaminodiphenyl, dialkyl-4,4'-diaminodiphenyls, dimethoxy-4,4'-diaminodiphenyl, diethoxy-4,4'-diaminodiphenyl, 4,4'-diaminodiphenyl ether, 3,4'-diaminodiphenyl ether, 4,4'-diaminodiphenylsulfone, 3,3'-diaminodiphenylsulfone, 4,4'-diaminobenzophenone, 3,3'-diaminobenzophenone, 1,3-bis(3-aminophenoxy)benzene, 1,3-bis(4-aminophenoxy)benzene, 1,4-bis(4-aminophenoxy)benzene, 4,4'-bis(4-aminophenoxy)biphenyl, bis(4-(3-aminophenoxy)phenyl)sulfone, bis(4-(4-aminophenoxy)phenyl)sulfone, 2,2-bis(4-(4-aminophenoxy)phenyl)propane, 2,2-bis(4-(4-aminophenoxy)phenyl)hexafluoropropane, 2,2-bis(4-(3-aminophenoxy)phenyl)propane, 2,2-bis(4-(3-aminophenoxy)phenyl)hexafluoropropane, 2,2-bis(4-(4-amino-2-trifluoromethylphenoxy)phenyl)hexafluoropropane, 2,2-bis(4-(3-amino-5-trifluoromethylphenoxy)phenyl)hexafluoropropane, 2,2-bis(4-aminophenyl)hexafluoropropane, 2,2-bis(3-aminophenyl)hexafluoropropane, 2,2-bis(3-amino-4-hydroxyphenyl)hexafluoropropane, 2,2-bis(3-amino-4-methylphenyl)hexafluoropropane, 4,4'-bis(4-aminophenoxy)octafluorobiphenyl, and 4,4'-diaminobenzanilide.

The polyamide type polymer compound can be produced by using a conventional polyamide production process without particular limitation. For example, the polymer compound represented by formula (7) can be produced by a direct polycondensation (dehydrocondensation) between the fluorine-containing dicarboxylic acid represented by formula (1) and the diamine represented by formula (3) in the presence of a condensing agent. Furthermore, it is also possible to use an amide-forming derivative of the fluorine-containing dicarboxylic acid. Herein, "amide-forming derivative" refers to a compound that easily forms an amide bond with a chemical reaction. In fact, the fluorine-containing dicarboxylic acid can be converted into an amide-forming derivative, such as acid halide (e.g., dichloride and dibromide of the dicarboxylic acid), dialkylester (e.g., dimethyl ester and diethyl ester of the dicarboxylic acid), ester having an active ester group (e.g., phenylester group, pyridylester group, succinimide ester group), and mixed acid anhydride. Then, it is possible to produce the polymer compound represented by formula (7) by reacting such amide-forming derivative with the diamine represented by formula (3). In this case, it is also possible to use a polymer dissolution accelerator (i.e., a metal salt such as lithium bromide and lithium chloride) and a dehydrating agent such as sulfuric acid.

The process and the conditions of polymerization (polycondensation) are not particularly limited. For example, it is possible to use a first process in which an amide-forming derivative of the fluorine-containing dicarboxylic acid and the diamine are dissolved or melted with each other at a temperature of 150° C. or higher to conduct the reaction without solvent. It is possible to use a second process in which the reaction is conducted in organic solvent at a high temperature (preferably 150° C. or higher). It is possible to use a third process in which the reaction is conducted in organic solvent at a temperature of −20 to 80° C.

It is simplest to use a process by mixing an amide-forming derivative of the fluorine-containing dicarboxylic acid represented by formula (1) with the diamine represented by formula (3) in organic solvent to conduct the polycondensation. The molar ratio of this amide-forming derivative to the diamine may be 0.5 to 1.5, preferably 0.8 to 1.2. Similar to normal polycondensation reactions, molecular weight of the obtained polymer becomes larger as this molar ratio gets closer to 1.

The organic solvent usable in the polycondensation is not particularly limited, as long as it can dissolve the both reactants. Its examples include the same organic solvents as those for producing the polyester type polymer compound. It is effective to conduct the reaction under coexistence of an acid acceptor (e.g., pyridine and triethylamine) with such organic solvent. In particular, if the above amide solvent is used, the solvent itself becomes an acid acceptor. With this, it is possible to obtain a polyamide resin that is high in degree of polymerization.

Polyamide Diol Type Polymer Compound

It is possible to conduct a polymerization by bringing the dicarboxylic acid (a fluorine-containing polymerizable monomer) represented by formula (1) into contact with a diaminodiol represented by formula (4),

in a given range of temperature, thereby obtaining a polyamide diol type polymer compound represented by formula (8).

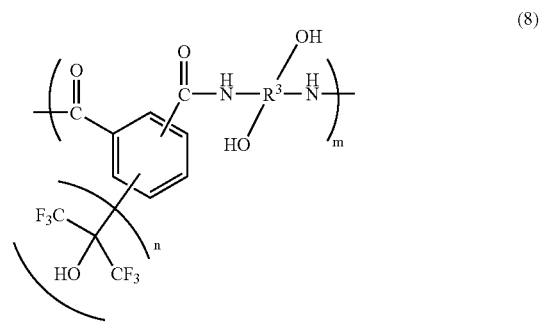

Specific examples of the diaminodiol represented by formula (4) include 2,4-diamino-1,5-benzenediol, 3,3'-dihydroxy-4,4'-diaminobiphenyl, 3,3'-diamino-4,4'-dihydroxybiphenyl, bis(3-amino-4-hydroxyphenyl)ketone, bis(3-amino-4-hydroxyphenyl)sulfide, bis(3-amino-4-hydroxyphenyl)ether, bis(3-hydroxy-4-aminophenyl)sulfone, 2,2-bis(3-amino-4-hydroxyphenyl)propane, 2,2-bis(3-hydroxy-4-aminophenyl)propane, bis(3-hydroxy-4-aminophenyl)methane, 2,2-bis(3-amino-4-hydroxyphenyl)hexafluoropropane, 2,2-bis(3-hydroxy-4-aminophenyl)hexafluoropropane and bis(3-amino-4-hydroxyphenyl)difluoromethane.

The polyamide diol type polymer compound can be produced by using a conventional polyamide diol production process without particular limitation. For example, the polymer compound represented by formula (8) can be produced by a direct polycondensation (dehydrocondensation) between the fluorine-containing dicarboxylic acid represented by formula (1) and the diaminodiol represented by formula (4) in the presence of a condensing agent. Furthermore, it is also possible to use an amide-forming derivative of the fluorine-containing dicarboxylic acid. In fact, the fluorine-containing dicarboxylic acid can be converted into an amide-forming derivative, such as acid halide (e.g., dichloride and dibromide of the dicarboxylic acid), dialkylester (e.g., dimethyl ester and diethyl ester of the dicarboxylic acid), ester having an active ester group (e.g., phenylester group, pyridylester group, succinimide ester group), and mixed acid anhydride. Then, it is possible to produce the polymer compound represented by formula (8) by reacting such amide-forming derivative with the diaminodiol represented by formula (4). In this case, it is also possible to use a polymer dissolution accelerator (i.e., a metal salt such as lithium bromide and lithium chloride) and a dehydrating agent such as sulfuric acid.

The process and the conditions of polymerization (polycondensation) are not particularly limited. They may be the same as those for producing the polyamide type polymer compound represented by formula (7), since elementary reaction of the polymerization is an amide-forming reaction. Furthermore, it is possible to use the same organic solvent as that for producing the polyamide type polymer compound.

It is possible to subject the polyamide diol type polymer compound to a dehydration, ring-closing reaction to convert it into a polybenzoxazole type polymer compound represented by formula (9).

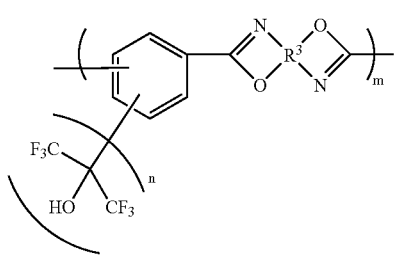

(9)

It is possible to use a conventional dehydration, ring-closing reaction without particular limitation. The cyclization can be conducted by various methods for accelerating the dehydration condition, such as heat, acid catalyst, and base catalyst. A heating ring-closing can be conducted at a temperature of 80-400° C., particularly preferably 150-350° C. If the ring-closing temperature is lower than 150° C., the ring closing rate may become too low. This may damage strength of the polybenzoxazole film. If it is higher than 350° C., the coated film may become colored or brittle. The acid catalyst may be selected from p-toluenesulfonic acid, methanesulfonic acid, etc. The base catalyst may be selected from triethylamine, pyridine, etc. If the polybenzoxazole after the ring closing is soluble in organic solvent, the ring closing can chemically be conducted by using a dehydration reagent (e.g., acetic anhydride) and an organic base (e.g., pyridine and triethylamine).

It is possible by the cyclization (ring-closing) to conduct a resin modification accompanied with considerable property changes, such as heat resistance improvement, solubility change, lowering of refractive index and dielectric constant, and occurrence of water repellency and oil repellency.

Highly Fluorinated Polyamide Type Polymer Compound

It is possible to conduct a polymerization by bringing the dicarboxylic acid (a fluorine-containing polymerizable monomer) represented by formula (1) into contact with a diaminodiol represented by formula (5),

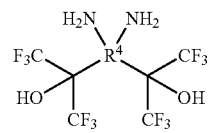

(5)

in a given range of temperature, thereby obtaining a highly fluorinated polyamide type polymer compound represented by formula (10).

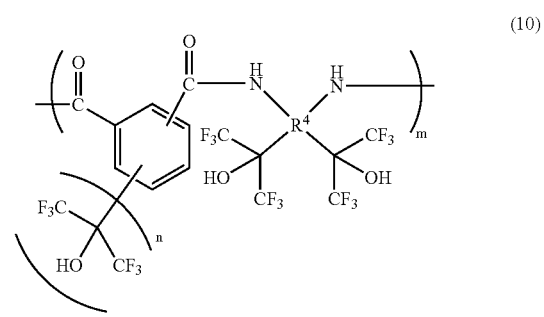

(10)

Specific examples of the diaminodiol represented by formula (5) having two hexafluoroisopropanol moieties include the following compounds.

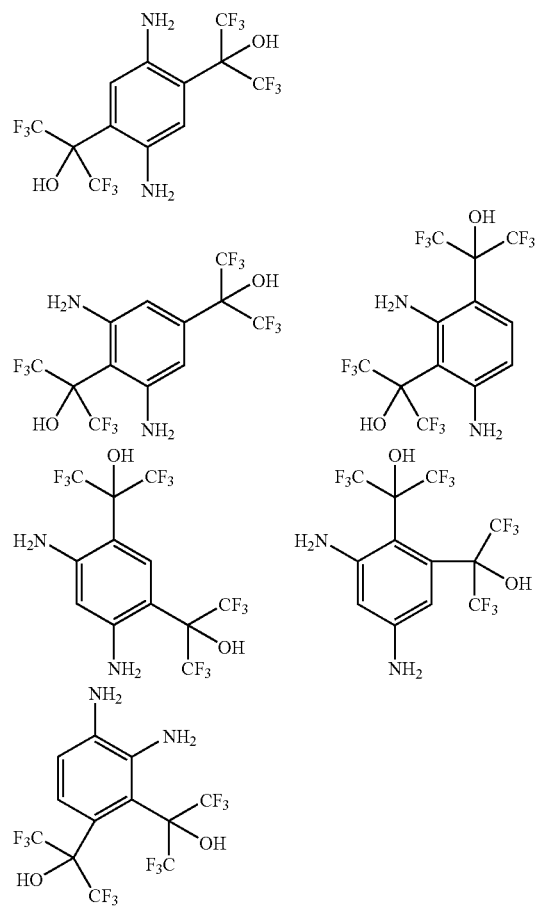

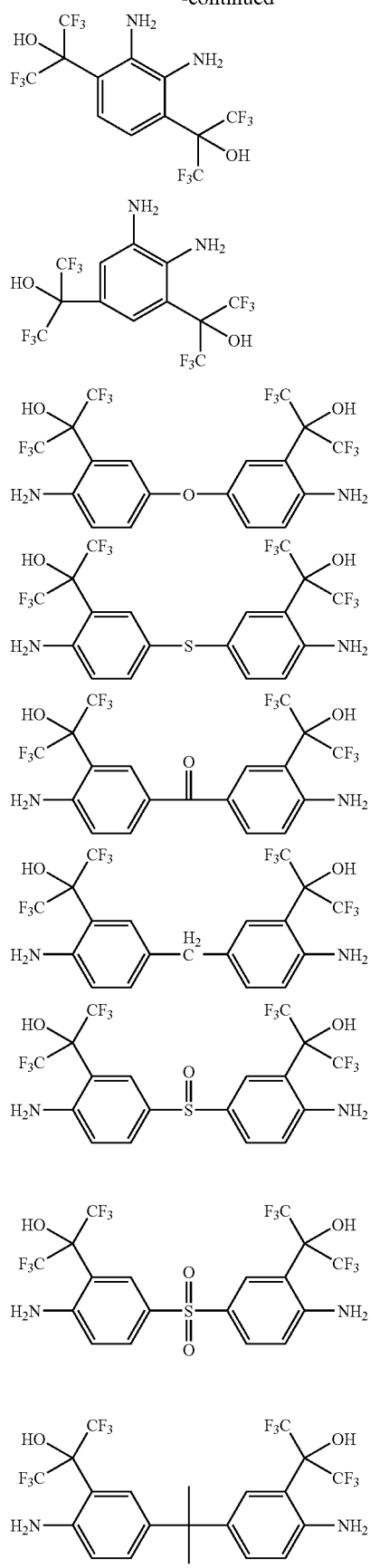
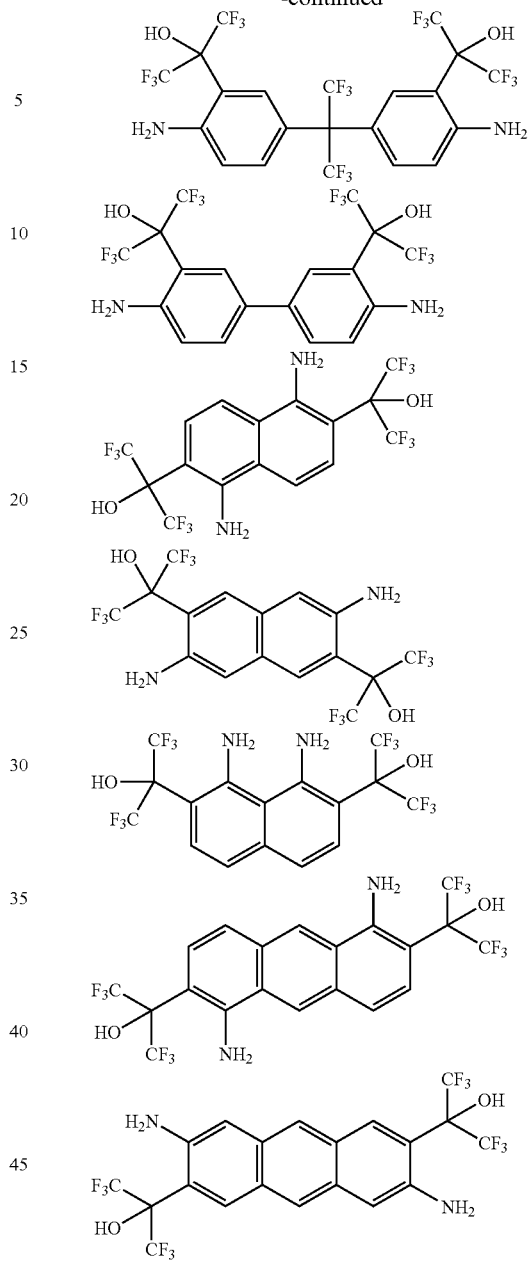

The highly fluorinated polyamide type polymer compound can be produced by using a conventional polyamide production process without particular limitation. For example, the polymer compound represented by formula (10) can be produced by a direct polycondensation (dehydrocondensation) between the fluorine-containing dicarboxylic acid represented by formula (1) and the diaminodiol represented by formula (5) in the presence of a condensing agent. Furthermore, it is also possible to use an amide-forming derivative of the fluorine-containing dicarboxylic acid. In fact, the fluorine-containing dicarboxylic acid can be converted into an amide-forming derivative, such as acid halide (e.g., dichloride and dibromide of the dicarboxylic acid), dialkylester (e.g., dimethyl ester and diethyl ester of the dicarboxylic acid), ester having an active ester group (e.g., phenylester group, pyridylester group, succinimide ester group), and mixed acid anhydride. Then, it is possible to produce the polymer compound represented by formula (10) by reacting such amide-forming derivative with the diaminodiol represented by formula (5). In this case, it is also possible to use a polymer dissolution accelerator (i.e., a metal salt such as lithium bromide and lithium chloride) and a dehydrating agent such as sulfuric acid.

The process and the conditions of polymerization (polycondensation) are not particularly limited. They may be the same as those for producing the polyamide type polymer compound represented by formula (7), since elementary reaction of the polymerization is an amide-forming reaction. Furthermore, it is possible to use the same organic solvent as that for producing the polyamide type polymer compound.

It is possible to subject the highly fluorinated polyamide type polymer compound to a dehydration, ring-closing reaction to convert it into a heterocyclic type polymer compound represented by formula (11)

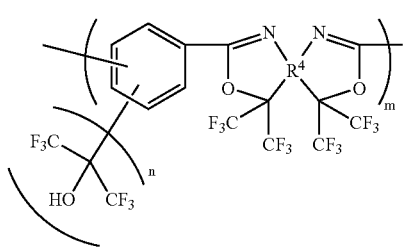
(11)

The conditions for conducting the dehydration, ring-closing reaction are not particularly limited. The cyclization can be conducted by various methods for accelerating the dehydration condition, such as heat, acid catalyst, and base catalyst. It is possible to achieve the dehydration, ring-closing under a milder condition than that for forming the oxazole ring of formula (9).

The heterocyclic polymer compound represented by formula (11) shows a lower dielectric constant, a lower water absorption and a higher transparency than the polybenzoxazole represented by formula (9) does, since the former contains hetero rings with trifluoromethyl groups.

It is possible to use the fluorine-containing polymer of the present invention in the form of varnish, where it is dissolved in organic solvent, powder, film, or solid. According to need, it is optional to add a suitable additive (e.g., oxidation stabilizer, filler, silane coupling agent, photosensitizing agent, photo polymerization initiator, and sensitizer) to the polymer obtained. In using the polymer in the form of varnish, it can be applied onto a substrate (e.g., glass, silicon wafer, metal, metal oxide, ceramic, and resin) by a normal method (e.g., spin coating, spraying, flow coating, impregnation coating, and brush coating).

Process for Producing 5-[2,2,2-Trifluoro-1-Hydroxy-1-(Trifluoromethyl)Ethyl]-1,3-Benzenedicarboxylic Acid As stated above, it is possible to obtain 4-[2,2,2-trifluoro-1-hydroxy-1-(trifluoromethyl)ethyl]-1,2-benzenedicarboxylic acid (see Journal of Organic Chemistry, 1965, Vol. 30, pp. 998-1001; U.S. Pat. No. 4,045,408; and the following reaction formula [2]) by a process in which a starting material of o-xylene is reacted with hexafluoroacetone to introduce a 2,2,2-trifluoro-1-hydroxy-1-(trifluoromethyl)ethyl group, and then the two methyl groups are oxidized by using an oxidizing agent (e.g., potassium permanganate). Similarly, it is possible to obtain 4-[2,2,2-trifluoro-1-hydroxy-1-(trifluoromethyl)ethyl]-1,3-benzenedicarboxylic acid (see Example 1 and the following reaction formula [3]) by replacing o-xylene with m-xylene. Similarly, it is possible to obtain 2-[2,2,2-trifluoro-1-hydroxy-1-(trifluoromethyl)ethyl]-1,4-benzenedicarboxylic acid (see Example 2 and the following reaction formula [4]) by replacing o-xylene with p-xylene.

Reaction Formula [2]
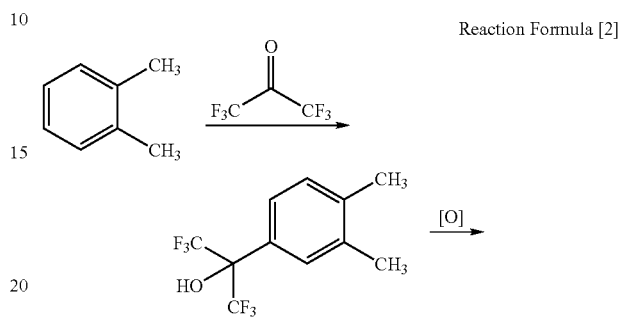

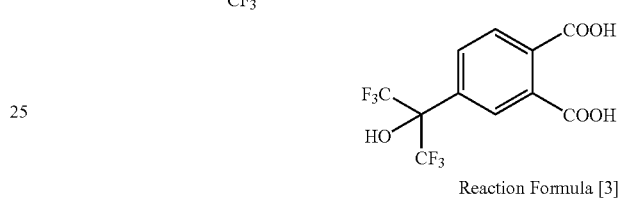

Reaction Formula [3]
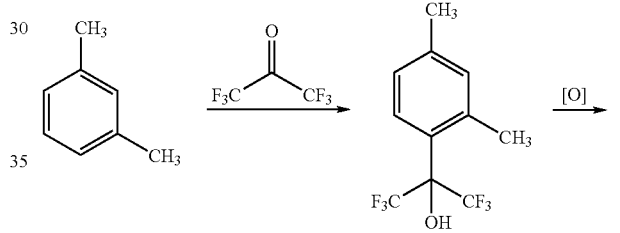

Reaction Formula [4]
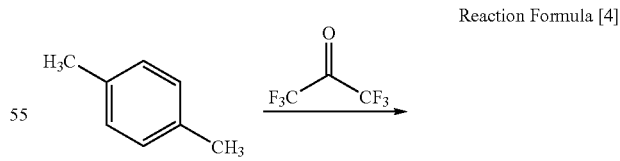

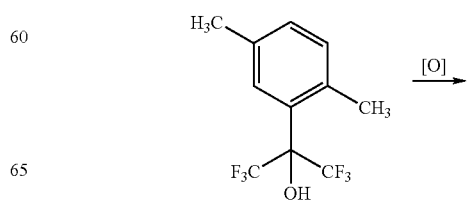

-continued

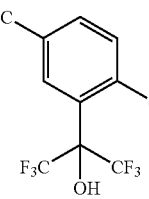

As stated above, however, it is difficult to synthesize linear polymers, such as polyester, polyamide and polybenzoxazole, particularly aromatic polymers oriented to heat resistance, from 4-[2,2,2-trifluoro-1-hydroxy-1-(trifluoromethyl)ethyl]-1,2-benzenedicarboxylic acid, which is obtained by Reaction Formula [2] and is not according to the present invention.

In contrast, each of 4-[2,2,2-trifluoro-1-hydroxy-1-(trifluoromethyl)ethyl]-1,3-benzenedicarboxylic acid and 2-[2,2,2-trifluoro-1-hydroxy-1-(trifluoromethyl)ethyl]-1,4-benzenedicarboxylic acid, which are respectively obtained by Reaction Formulas [3] and [4] and are according to the present invention, has a higher linearity and thereby suitably functions as a structural unit of various polymers.

From the viewpoint of symmetry, however, it is considered that 5-[2,2,2-trifluoro-1-hydroxy-1-(trifluoromethyl)ethyl]-1,3-benzenedicarboxylic acid represented by the following formula,

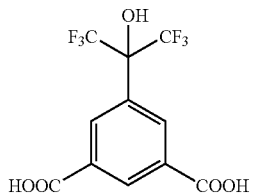

is a more superior structural unit. The process for producing a compound having such structure has not been known up to now. This compound cannot be produced by a process in which m-xylene is reacted with hexafluoroacetone (see Reaction Formula [3]), due to the problem of orientation.

As a result of further research, we have found a process for producing the target 5-[2,2,2-trifluoro-1-hydroxy-1-(trifluoromethyl)ethyl]-1,3-benzenedicarboxylic acid by using a trihalobenzene as the starting material by referring to Journal of Organometallic Chemistry, Vol. 215, 1981, pp. 281-291.

This process includes the steps of:
(a) reacting a 1,3,5-trihalobenzene represented by formula (13),

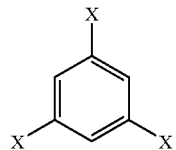

(13)

wherein X represents a halogen that is fluorine, chlorine, bromine or iodine, trifluoromethanesulfonate group, $C_1$-$C_4$ alkylsulfonate group, or arylsulfonate group,
with an alkylmagnesium halide, metallic magnesium or alkyllithium;

(b) treating a product of the step (a) with hexafluoroacetone, thereby obtaining 5-[2,2,2-trifluoro-1-hydroxy-1-(trifluoromethyl)ethyl]-1,3-dihalobenzene represented by formula (12),

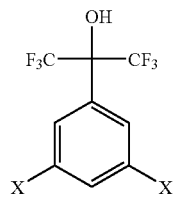

(12)

wherein X is defined as above, and (c) carbonylating the 5-[2,2,2-trifluoro-1-hydroxy-1-(trifluoromethyl)ethyl]-1,3-dihalobenzene into 5-[2,2,2-trifluoro-1-hydroxy-1-(trifluoromethyl)ethyl]-1,3-benzenedicarboxylic acid.

The steps (a) and (b) are as shown in the following Scheme [1].

Scheme 1

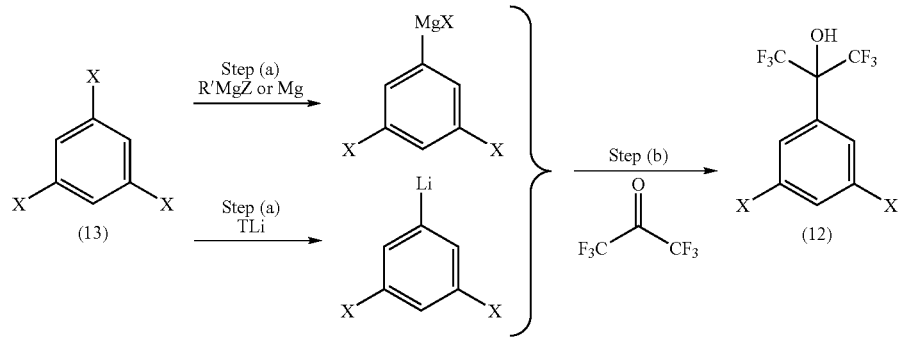

Specific examples of the 1,3,5-trihalobenzene used in the step (a) include 1,3,5-trifluorobenzene, 1,3,5-tricholorobenzene, 1,3,5-tribromobenzene, 1,3,5-triiodobenzene, 1,3,5-tris(trifluoromethanesulfonyl)benzene, 1,3,5-tri(methanesulfonyl)benzene, 1,3,5-tri(benzenesulfonyl)benzene, and 1,3,5-tri(p-tosylsulfonyl)benzene. Of these, 1,3,5-tricholorobenzene, 1,3,5-tribromobenzene and 1,3,5-triiodobenzene are preferable, and 1,3,5-tribromobenzene is particularly preferable.

The step (a) may be conducted by a first reaction in which the 1,3,5-trihalobenzene is reacted with an alkylmagnesium halide represented by formula (14)

R'MgZ　(14)

wherein R' represents an alkyl group, and Z represents a halogen that is chlorine, bromine or iodine. The alkyl group R' may be straight-chain or branched and may be a $C_1$-$C_8$ alkyl group. Its specific examples include ethyl group, propyl group, isopropyl group, butyl group, isobutyl group, t-butyl group, pentyl group, hexyl group, heptyl group, octyl group, and 2-ethylhexyl group. The halogen Z is preferably a chlorine atom or bromine atom.

The first reaction may be conducted in a suitable solvent, preferably under an inert gas atmosphere, to obtain 3,5-dihalophenylmagnesium halide (see Scheme 1).

The amount of the alkylmagnesium halide by mol may be 0.3 to 5 times, preferably 1 to 2 times, that of the 1,3,5-trihalobenzene represented by formula (13).

In the first reaction, the solvent is preferably an ether series solvent. Its specific examples include diethyl ether, diisopropyl ether, t-butoxymethane, ethylene glycol dimethyl ether, tetrahydrofuran, and dioxane. The amount of the solvent by volume may be 0.5 to 10 times, preferably 1 to 5 times, that of the 1,3,5-trihalobenzene represented by formula (13). The inert gas is preferably nitrogen gas or argon gas.

The reaction temperature for conducting the first reaction may be in a range of 0° C. to around the reflux temperature of the solvent, preferably 0° C. to 65° C., more preferably 10° C. to 40° C.

The reaction time for conducting the first reaction is not particularly limited. The optimum reaction time may vary depending on temperature and the amount of the substrate used. Therefore, it is preferable to conduct the reaction, while monitoring progress of the reaction by a general-purpose analytical means, such as gas chromatography, and to terminate the first reaction after confirming that the raw material has sufficiently been consumed.

The alkylmagnesium halide may be a commercial product or one produced upon conducting the first reaction.

The step (a) may be conducted by a second reaction in which the 1,3,5-trihalobenzene represented by formula (13) is reacted with metallic magnesium in a suitable solvent, preferably under an inert gas atmosphere, to obtain 3,5-dihalophenylmagnesium halide (see Scheme 1).

The metallic magnesium may be in any form such as bulky form, tape form, foil form, flake form, shave form, or powder form. From the point of reactivity, it is preferably flake form, shave form or powder form, particularly preferably powder form. The amount of the metallic magnesium by mol may be 0.8 to 5 times, preferably 1 to 2 times, that of the 1,3,5-trihalobenzene represented by formula (13).

In the second reaction, the solvent is preferably an ether series solvent. Its specific examples include diethyl ether, diisopropyl ether, t-butoxymethane, ethylene glycol dimethyl ether, tetrahydrofuran, and dioxane. The amount of the solvent by volume may be 0.5 to 10 times, preferably 1 to 5 times, that of the 1,3,5-trihalobenzene represented by formula (13). The inert gas is preferably nitrogen gas or argon gas.

The reaction temperature for conducting the second reaction may be in a range of 0° C. to around the reflux temperature of the solvent, preferably 0° C. to 100° C., more preferably 10° C. to 80° C.

The reaction time for conducting the second reaction is not particularly limited. The optimum reaction time may vary depending on temperature and the amount of the substrate used. Therefore, it is preferable to conduct the reaction, while monitoring progress of the reaction by a general-purpose analytical means, such as gas chromatography, and to terminate the second reaction after confirming that the raw material has sufficiently been consumed.

The step (a) may be conducted by a third reaction in which the 1,3,5-trihalobenzene is reacted with an alkyllithium represented by formula (16),

TLi　(15)

where T represents an alkyl group. This alkyl group may be straight-chain or branched and may be a $C_1$-$C_6$ alkyl group. Its specific examples include methyl group, ethyl group, propyl group, isopropyl group, butyl group, isobutyl group, t-butyl group, pentyl group, and hexyl group.

The third reaction may be conducted in a suitable solvent, preferably under an inert gas atmosphere, to obtain 3,5-dihalophenyllithium (see Scheme 1).

The amount of the alkyllithium by equivalent may be 0.8 to 1.5 times, preferably 1 to 1.2 times, that of the 1,3,5-trihalobenzene represented by formula (13).

In the third reaction, specific examples of the solvent include ethers (e.g., diethyl ether, tetrahydrofuran, dioxane, butyl methyl ether, diisopropyl ether, and ethylene glycol dimethyl ether), alkanes (e.g., n-pentane, n-hexane, n-heptane, and n-octane), and aromatics (e.g., benzene, toluene, and xylene).

These solvents may be used singly or in a mixture of at least two. The amount of the solvent by volume may be 0.5 to 10 times, preferably 1 to 5 times, that of the 1,3,5-trihalobenzene represented by formula (13). The inert gas is preferably nitrogen gas or argon gas.

The reaction temperature for conducting the third reaction may be −150° C. to 200° C., preferably −110° C. to around the reflux temperature of the solvent.

The reaction time for conducting the third reaction is not particularly limited. The optimum reaction time may vary depending on temperature and the amount of the substrate used. Therefore, it is preferable to conduct the reaction, while monitoring progress of the reaction by a general-purpose analytical means, such as gas chromatography, and to terminate the third reaction after confirming that the raw material has sufficiently been consumed.

The alkyllithium may be a commercial product or one produced upon conducting the third reaction.

The step (b) is conducted by reacting an intermediate obtained by the step (a) with hexafluoroacetone (see Scheme 1).

The intermediate obtained by each of the first to third reactions of the step (a) is a highly reactive, unstable substance. Therefore, it is normal to subject the reaction liquid after the step (a) to the step (b) without conducting a purification to isolate the intermediate.

In the step (b), hexafluoroacetone (boiling point: −28° C.) may be bubbled as gas into the reaction liquid or may be added as liquid by cooling. It is, however, necessary to use a hexafluoroacetone that is sufficiently dry and contains no water. Its hydrate is of no use.

In the case of using hexafluoroacetone as gas, it is preferable to use an apparatus (a cooling apparatus or sealed reactor) for preventing leak of hexafluoroacetone. The apparatus is particularly preferably a sealed reactor.

The step (b) may be conducted at a temperature of −200° C. to 50° C., preferably −150° C. to room temperature, particularly preferably −100° C. to room temperature. If it is lower than −200° C., it may be difficult to conduct the reaction. If it is higher than 50° C., side reactions may occur.

It is preferable to conduct the step (b) by using solvent. The solvent to be used is not particularly limited, as long as it is not involved in the reaction. As stated above, it is possible to easily conduct the step (b) by adding hexafluoroacetone to the reaction liquid after the step (a). Therefore, it is preferable to use the solvent itself used in the step (a).

The reaction time for conducting the step (b) is not particularly limited. The optimum reaction time may vary depending on temperature and the amount of the substrate used. Therefore, it is preferable to conduct the reaction, while monitoring progress of the reaction by a general-purpose analytical means, such as gas chromatography, and to terminate the reaction after confirming that the raw material has sufficiently been consumed.

After the step (b), it is possible to obtain 5-[2,2,2-trifluoro-1-hydroxy-1-(trifluoromethyl)ethyl]-1,3-dihalobenzene represented by formula (12) by a normal means such as extraction, distillation or crystallization. According to need, it can be purified by column chromatography, recrystallization, etc.

The step (c) is conducted by carbonylating 5-[2,2,2-trifluoro-1-hydroxy-1-(trifluoromethyl)ethyl]-1,3-dihalobenzene, which is represented by formula (12), into 5-[2,2,2-trifluoro-1-hydroxy-1-(trifluoromethyl)ethyl]-1,3-benzenedicarboxylic acid. This carbonylation may be conducted as shown in Scheme 2.

group, isopropyl group, butyl group, isobutyl group, t-butyl group, pentyl group, hexyl group, heptyl group, octyl group, and 2-ethylhexyl group. The halogen Z is preferably a chlorine atom or bromine atom.

The first reaction may be conducted in a suitable solvent, preferably under an inert gas atmosphere, to obtain a Grignard reagent (see Scheme 2).

The amount of the alkylmagnesium halide by mol may be 1 to 10 times, preferably 2 to 4 times, that of the 5-[2,2,2-trifluoro-1-hydroxy-1-(trifluoromethyl)ethyl]-1,3-dihalobenzene represented by formula (12).

In the first reaction, the solvent is preferably an ether series solvent. Its specific examples include diethyl ether, diisopropyl ether, t-butoxymethane, ethylene glycol dimethyl ether, tetrahydrofuran, and dioxane. The amount of the solvent by volume may be 0.5 to 10 times, preferably 1 to 5 times, that of the 5-[2,2,2-trifluoro-1-hydroxy-1-(trifluoromethyl)ethyl]-1,3-dihalobenzene represented by formula (12). The inert gas is preferably nitrogen gas or argon gas.

The reaction temperature for conducting the first reaction may be in a range of 0° C. to around the reflux temperature of the solvent, preferably 0° C. to 65° C., more preferably 10° C. to 40° C. The reaction time may be 1 to 48 hours. The alkylmagnesium halide may be a commercial product or one produced upon conducting the first reaction.

The step (d) may be conducted by a second reaction in which the 5-[2,2,2-trifluoro-1-hydroxy-1-(trifluoromethyl) ethyl]-1,3-dihalobenzene represented by formula (12) is

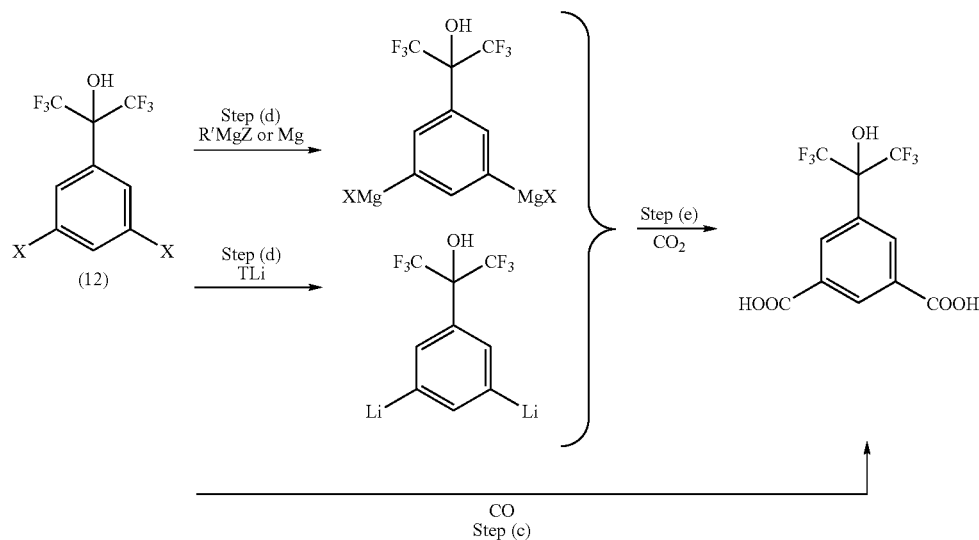

Scheme 2

As shown in Scheme 2, the step (c) may be conducted by two steps of (d) and (e).

The step (d) may be conducted by a first reaction in which 5-[2,2,2-trifluoro-1-hydroxy-1-(trifluoromethyl)ethyl]-1,3-dihalobenzene, which is represented by formula (12), is reacted with an alkylmagnesium halide represented by formula (14)

R'MgZ             (14)

wherein R' represents an alkyl group, and Z represents a halogen that is chlorine, bromine or iodine. The alkyl group R' may be straight-chain or branched and may be a $C_1$-$C_8$ alkyl group. Its specific examples include ethyl group, propyl reacted with metallic magnesium in a suitable solvent, preferably under an inert gas atmosphere, to obtain a Grignard reagent (see Scheme 2).

The metallic magnesium may be in any form such as bulky form, tape form, foil form, flake form, shave form, or powder form. From the point of reactivity, it is preferably flake form, shave form or powder form, particularly preferably powder form. The amount of the metallic magnesium by mol may be 1 to 10 times, preferably 2 to 5 times, that of the 5-[2,2,2-trifluoro-1-hydroxy-1-(trifluoromethyl)ethyl]-1,3-dihalobenzene represented by formula (12).

In the second reaction, the solvent is preferably an ether series solvent. Its specific examples include diethyl ether, diisopropyl ether, t-butoxymethane, ethylene glycol dimethyl ether, tetrahydrofuran, and dioxane. The amount of the solvent by volume may be 0.5 to 10 times, preferably 1 to 5 times, that of the 5-[2,2,2-trifluoro-1-hydroxy-1-(trifluoromethyl)ethyl]-1,3-dihalobenzene represented by formula (12). The inert gas is preferably nitrogen gas or argon gas.

The reaction temperature for conducting the second reaction may be in a range of 0° C. to around the reflux temperature of the solvent, preferably 0° C. to 100° C., more preferably 10° C. to 80° C. The reaction time may be 1 to 48 hours.

The step (d) may be conducted by a third reaction in which the 5-[2,2,2-trifluoro-1-hydroxy-1-(trifluoromethyl)ethyl]-1,3-dihalobenzene represented by formula (12) is reacted with an alkyllithium represented by formula (16), $$TLi \quad (15)$$

where T represents an alkyl group. This alkyl group may be straight-chain or branched and may be a $C_1$-$C_6$ alkyl group. Its specific examples include methyl group, ethyl group, propyl group, isopropyl group, butyl group, isobutyl group, t-butyl group, pentyl group, and hexyl group.

The third reaction may be conducted in a suitable solvent, preferably under an inert gas atmosphere, to obtain an organic lithium reagent (see Scheme 2).

The amount of the alkyllithium by equivalent may be 1 to 10 times, preferably 2 to 5 times, that of the 5-[2,2,2-trifluoro-1-hydroxy-1-(trifluoromethyl)ethyl]-1,3-dihalobenzene represented by formula (12).

In the third reaction, specific examples of the solvent include ethers (e.g., diethyl ether, tetrahydrofuran, dioxane, butyl methyl ether, diisopropyl ether, and ethylene glycol dimethyl ether), alkanes (e.g., n-pentane, n-hexane, n-heptane, and n-octane), and aromatics (e.g., benzene, toluene, and xylene).

These solvents may be used singly or in a mixture of at least two. The amount of the solvent by volume may be 0.5 to 10 times, preferably 1 to 5 times, that of the 5-[2,2,2-trifluoro-1-hydroxy-1-(trifluoromethyl)ethyl]-1,3-dihalobenzene represented by formula (12). The inert gas is preferably nitrogen gas or argon gas.

The reaction temperature for conducting the third reaction may be −150° C. to 200° C., preferably −110° C. to around the reflux temperature of the solvent. The reaction time may be 1 to 48 hours. The alkyllithium may be a commercial product or one produced upon conducting the third reaction.

The step (e) is a carbonylation of an intermediate (i.e., the Grignard reagent or organic lithium reagent) obtained by the step (d) into the target 5-[2,2,2-trifluoro-1-hydroxy-1-(trifluoromethyl)ethyl]-1,3-benzenedicarboxylic acid by carbon dioxide as a carbonylation agent (see Scheme 2).

In the step (e), the form of carbon dioxide under ordinary temperature and ordinary pressure is not particularly limited, and it may take a gas or solid form. A skilled person in the art can select a suitable form.

In the case of replacing the atmosphere of the reaction system with carbon dioxide in the form of gas, the reaction can be conducted under a pressurized condition. In this case, a reactor is charged with the reaction liquid obtained by the step (e), followed by tightly closing the reactor.

In the case of using carbon dioxide (dry ice) in the form of solid, the reaction can be conducted under ordinary pressure due to its easy handling.

The carbonylation is conducted by heating with or without stirring. In the case of conducting the reaction under pressurized condition, the pressure may be 0.1 to 1.2 kPa, preferably 0.5 to 1.0 kPa, more preferably 0.5 to 0.8 kPa. If it is lower than 0.1 kPa, the reaction may not proceed sufficiently, thereby causing low yield or necessity of a long time to complete the reaction due to low reaction rate. Even if it is higher than 1.2 kPa, there occurs almost no change in reaction rate and yield of the target product in the carbonylation. Therefore, it is not preferable.

As the reactor for conducting the reaction under pressurized condition, it is possible to use a metal container such as stainless steel, Hastelloy and Monel metal. In the case of conducting the reaction under ordinary pressure, a skilled person in the art can suitably select the reactor.

The reaction temperature upon adding carbon dioxide in the form of gas or solid (dry ice) may be −150° C. to 200° C., preferably −110° C. to around the reflux temperature of the solvent used.

As an alternative to the two steps (d) and (e), the step (c) may be conducted by one step in which 5-[2,2,2-trifluoro-1-hydroxy-1-(trifluoromethyl)ethyl]-1,3-dihalobenzene represented by formula (12) is reacted with carbon monoxide as a carbonylation agent in the presence of a palladium catalyst and a basic substance (see Scheme 2). This reaction is described in detail in the following.

Specific preferable examples of the palladium catalyst include palladium-carried activated carbon, palladium chloride, palladium acetate, tetrakis(triphenylphosphine)palladium, bis(dibenzylideneacetonato)palladium, $PdCl_2[P(o-Me-Ph)_3]_2$, $PdCl_2[P(m-Me-Ph)_3]_2$, $PdCl_2[P(p-Me-Ph)_3]_2$, $PdCl_2[(PMe)_3]_2$, $PdBr_2[(PPh)_3]_2$, $PdCl_2[P(Ph)_2CH_2CH_2P(Ph)_2]$, $PdCl_2[P(Ph)_2CH_2CH_2CH_2CH_2P(Ph)_2]$, $PdCl_2(PhCN)_2$, $Pd(CO)(PPh_3)_3$, $PhPdI(PPh_3)_2$, $PhPdBr(PPh_3)_2$, $PhPdBr(PMePh_2)_2$, $PhCl_2(PMePh_2)_2$, $PhCl_2(PEt_2Ph)_2$, $PhCl_2(PMe_2Ph)_2$, $Pd_2Br_4(PPh_3)_2$, and $PdCl_2[P(Ph)_3]_2$, where Ph represents a phenyl group, Me a methyl group, Et an ethyl group, o-ortho substitution, m-meta substitution, and p-para substitution.

Each of these palladium catalysts shows a satisfactory catalytic activity. It is economically particularly preferable to use a bivalent palladium complex, such as palladium chloride, palladium acetate, $PdCl_2[P(Ph)_3]_2$, and $PdCl_2[P(Ph)_2CH_2CH_2CH_2CH_2P(Ph)_2]$, which have low prices and are easy in handling.

The amount of the palladium catalyst may be 0.00001 to 0.2 moles, preferably 0.001 to 0.1 moles, more preferably 0.001 to 0.05 moles, per mol of 5-[2,2,2-trifluoro-1-hydroxy-1-(trifluoromethyl)ethyl]-1,3-dihalobenzene represented by formula (12).

It is particularly preferable to use a trivalent phosphorus compound as a promoter to maintain activity of the palladium catalyst. Herein, the promoter refers to a substance that is added in a small amount to increase activity or selectivity of the catalyst.

A preferable compound as the promoter is represented by formula (16), $$R^5—(R^6—)P—R^7 \quad (16)$$

wherein $R^5$, $R^6$ and $R^7$ represent the same or different alkyl groups, aryl groups, alkoxy groups, aryloxy groups, or halogen atoms. Its specific examples include tri-n-butylphosphine, triethylphosphine, triphenylphosphine, tri-o-tolylphosphine, tri-m-tolylphosphine, tri-p-tolylphosphine, tri-o-tolylphosphite, and phosphorus trichloride.

Another preferable compound as the promoter is a phosphine represented by formula (17), $$(R^5)_2P-Q-P(R^6)_2 \quad (17)$$

wherein $R^5$ and $R^6$ are defined as in formula (16), and Q represents an alkylene group —$(CH_2)_m$— where m represents an integer of 1-8, preferably 1-4. Specific examples of this phosphine include 1,1'-bis(diphenylphosphino)ferrocene, 1,4-bis(diphenylphosphino)butane, 1,3-bis(diphenylphosphino)propane, 1,2-bis(diphenylphosphinoethane.

The amount of the trivalent phosphorus compound may be 0.5 to 50 moles per mol of the palladium catalyst. Herein, the trivalent phosphorus compound may be in a first form that is a free compound by itself or in a second form (e.g., $PdCl_2[P(Ph)_3]_2$) in which it has already been incorporated as a ligand into a palladium catalyst. It is optional to use the first and second forms at the same time.

The basic substance used in the step (c) is not particularly limited, but it is preferably a basic substance such that pH becomes 8 or greater. Its specific examples include inorganic bases (e.g., ammonia, sodium carbonate, sodium hydrogencarbonate, sodium hydroxide, potassium carbonate, potassium hydrogencarbonate, and potassium hydroxide), and organic bases such as tertiary amines (e.g., trimethylamine, triethylamine, tripropylamine, and tributylamine), secondary amines (e.g., diethylamine and dipropylamine), and primary amines (e.g., propylamine and butylamine). Of these, a preferable one is an organic amine that is a base having a middle strength. Its specific examples include methylamine, ethylamine, isopropylamine, n-butylamine, dimethylamine, diethylamine, triethylamine, di-isopropylethylamine, di-n-butylamine, tri-n-butylamine, tetramethylethylenediamine, N,N-dimethylaniline, N,N-diethylaniline, pyridine, lutidine, 2-methylpyridine, N-methylmorpholine, pyperidine, pyrrolydine, morpholine, dibutylamine, and diisopropylamine. Of these, triethylamine is particularly preferable.

The amount of the basic substance may be 1-50 moles, preferably 1-20 moles, more preferably 1-10 moles, per mol of 5-[2,2,2-trifluoro-1-hydroxy-1-(trifluoromethyl)ethyl]-1,3-dihalobenzene represented by formula (12). The reaction is conducted normally in an inert gas such as nitrogen or argon. In general, the reaction temperature may be −50° C. to 160° C., preferably −10° C. to 100° C., more preferably −5° C. to 50° C.

The step (c) as one step is conducted preferably in the presence of solvent. The solvent is not particularly limited as long as it is not involved in the reaction. Its specific examples include aromatics (e.g., n-pentane, n-hexane, n-heptane, and n-octane), ethers (e.g., diethyl ether, tetrahydrofuran, and dioxane), halogenated hydrocarbons (e.g., dichloromethane and chloroform), alkylketones (e.g., acetone), alcohols (e.g., methanol, ethanol, ethylene glycol, diethylene glycol, and glycerol), aprotic polar solvents (e.g., acetonitrile, N,N-dimethylformamide (DMF), dimethylsufoxide (DMSO), and hexamethylphosphoric triamide (HMPA)) and water. Of these, preferable ones are ethers (e.g., diethyl ether, tetrahydrofuran, and dioxane) and alcohols (e.g., methanol, ethanol, ethylene glycol, diethylene glycol, and glycerol). A particularly preferable one is water. These solvents may be used singly or in combination of at least two. The amount of the solvent by volume may be 0.5 to 10 times, preferably 1 to 7 times, that of 5-[2,2,2-trifluoro-1-hydroxy-1-(trifluoromethyl)ethyl]-1,3-dihalobenzene represented by formula (12).

The reaction temperature of the step (c) as one step is not particularly limited. It may be −50° C. to 200° C., preferably −10° C. to 180° C., more preferably −5° C. to 150° C.

As stated above, carbon monoxide is used as a carbonylation agent. The reaction can be conducted under pressurized condition in the case of replacing atmosphere of the reaction system with carbon monoxide. The reaction is conducted by firstly charging the reactor with 5-[2,2,2-trifluoro-1-hydroxy-1-(trifluoromethyl)ethyl]-1,3-dihalobenzene represented by formula (12), palladium catalyst, basic substance and solvent and then tightly closing the reactor.

The carbonylation is conducted by heating with or without stirring. In the case of conducting the reaction under pressurized condition, the pressure may be 0.1 to 1.2 kPa, preferably 0.5 to 1.0 kPa, more preferably 0.5 to 0.8 kPa. If it is lower than 0.1 kPa, the reaction may not proceed sufficiently, thereby causing low yield or necessity of a long time to complete the reaction due to low reaction rate. Even if it is higher than 1.2 kPa, there occurs almost no change in reaction rate and yield of the target product in the carbonylation. Therefore, it is not preferable.

As the reactor for conducting the reaction under pressurized condition, it is possible to use a metal container such as stainless steel, Hastelloy and Monel metal.

The post treatment after the reaction of the step (c) by the above-described two steps (d) and (e) or by the above-described one step (c) may be conducted by a normal post treatment of organic syntheses. For example, it is possible to conduct the post treatment by adding the reaction liquid to a hydrochloric acid aqueous solution, followed by extraction with an organic solvent (e.g., ethyl acetate, toluene, and methylene chloride), then removing water from the organic layer with dehydrator or the like, and then distilling the solvent off, thereby obtaining a crude product of 5-[2,2,2-trifluoro-1-hydroxy-1-(trifluoromethyl)ethyl]-1,3-benzenedicarboxylic acid.

It is possible to conduct a further post treatment as a particularly preferable embodiment by adding an inorganic base (e.g., sodium hydroxide) aqueous solution to the above crude product to dissolve it as a benzoate in the aqueous solution, followed by extracting organic impurities with an organic solvent (e.g., hexane and heptane), then making the remaining aqueous solution acidic by using an acid (e.g., hydrochloric acid), then extraction with an organic solvent (e.g., ethyl acetate, toluene, and methylene chloride), then removing water with dehydrator or the like, and then distilling the solvent off, thereby obtaining a purified product of 5-[2,2,2-trifluoro-1-hydroxy-1-(trifluoromethyl)ethyl]-1,3-benzenedicarboxylic acid.

The following nonlimitative examples are illustrative of the present invention.

Example 1

Production of 4-[2,2,2-Trifluoro-1-Hydroxy-1-(Trifluoromethyl)Ethyl]-1,3-Benzenedicarboxylic Acid (Dicarboxylic Acid 1)

A 1 L reactor was charged under nitrogen with 100.0 g (0.94 mol) of m-xylene and 6.3 g (0.047 mol/0.05 eq) of aluminum chloride, followed by adjusting the inside temperature to 10° C. Then, 164.2 g (0.99 mol/1.05 eq) of hexafluoroacetone was introduced in a temperature range of 10-25° C. After the introduction, stirring was conducted at room temperature for 1 hr. Then, 100 mL of 10% hydrochloric acid was added. The resulting aqueous layer was extracted two times with 40 mL of chloroform. The resulting organic layers were combined together, followed by removing water with anhydrous magnesium sulfate, filtration, concentration, and vacuum distillation, thereby obtaining 227.6 g of 4-[2,2,2-trifluoro-1-hydroxy-1-(trifluoromethyl)ethyl]-1,3-dimethylbenzene represented by the following formula. Upon this, purity was 95%, and yield was 84%.

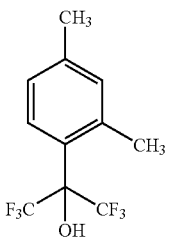

The properties of the obtained 4-[2,2,2-trifluoro-1-hydroxy-1-(trifluoromethyl)ethyl]-1,3-dimethylbenzene were as follows.

$^1$H NMR (DMSO-d$_6$): δ 8.37 (s, 1H), 7.34 (d, J=8.0 Hz, 1H), 7.12-7.06 (m, 2H), 2.52 (s, 3H), 2.26 (s, 3H).
$^{19}$F NMR (DMSO-d$_6$): δ −72.1 (s, 6F, CF$_3$).

A 300 mL reactor was charged with 10.0 g (36.7 mmol) of the obtained 4-[2,2,2-trifluoro-1-hydroxy-1-(trifluoromethyl)ethyl]-1,3-dimethylbenzene (purity: 95%) and 150 mL of 0.15N NaOH, followed by heating to 85° C. Then, 26.1 g (165.3 mmol/4.7 eq) of potassium permanganate was gradually added by spending 1 hr, followed by stirring at 90° C. for 4 hr. After the reaction, 11 mL of concentrated hydrochloric acid was added, followed by discoloring with sodium sulfite and extraction with 200 mL of diisopropyl ether. Furthermore, the aqueous layer was extracted two times with 50 mL of diisopropyl ether. The combined organic layer was dehydrated with anhydrous magnesium sulfate, followed by filtration, concentration and drying, thereby obtaining a pale yellow powder. To the obtained pale yellow powder 30 mL of toluene and 4 mL of acetonitrile were added, followed by reflux and cooling to conduct recrystallization, thereby obtaining 6.1 g of the target 4-[2,2,2-trifluoro-1-hydroxy-1-(trifluoromethyl)ethyl]-1,3-benzenedicarboxylic acid represented by the following formula. Upon this, yield was 50%, and purity was 99.5%.

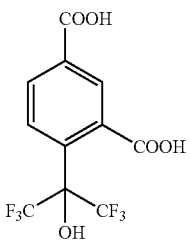

The properties of the obtained 4-[2,2,2-trifluoro-1-hydroxy-1-(trifluoromethyl)ethyl]-1,3-benzenedicarboxylic acid were as follows.

$^1$H NMR (DMSO-d$_6$): δ 8.64 (dd, J=8.0 and 1.2 Hz, 1H), 8.61 (s, 1H), 8.28 (d, J=8.0 Hz, 1H).
$^{13}$C NMR (DMSO-d$_6$): δ 165.83 (s), 165.34 (s), 139.80 (s), 138.45 (s), 137.56 (s), 128.62 (s), 125.90 (s), 125.77 (s), 121.15 (q, J=284.7 Hz), 81.67 (sept, J=32.9 Hz).
$^{19}$F NMR (DMSO-d$_6$): δ −73.7 (s, 6F, CF$_3$).

Example 2

Production of 2-[2,2,2-Trifluoro-1-Hydroxy-1-(Trifluoromethyl)Ethyl]-1,4-Benzenedicarboxylic Acid (Dicarboxylic Acid 2)

A 1 L reactor was charged under nitrogen with 200.0 g (1.88 mol) of p-xylene and 12.5 g (0.094 mol/0.06 eq) of aluminum chloride, followed by adjusting the inside temperature to 18° C. Then, 327.7 g (1.97 mol/1.06 eq) of hexafluoroacetone was introduced in a temperature range of 18-25° C. After the introduction, stirring was conducted at room temperature for 3 hr. Then, 200 mL of 10% hydrochloric acid was added. The resulting aqueous layer was extracted two times with 50 mL of chloroform. The resulting organic layers were combined together, followed by removing water with anhydrous magnesium sulfate, filtration, concentration, and vacuum distillation, thereby obtaining 451.3 g of 2-[2,2,2-trifluoro-1-hydroxy-1-(trifluoromethyl)ethyl]-1,4-dimethylbenzene represented by the following formula. Upon this, purity was 92%, and yield was 81%.

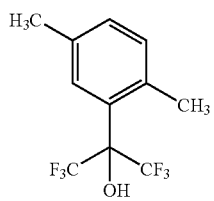

The properties of the obtained 2-[2,2,2-trifluoro-1-hydroxy-1-(trifluoromethyl)ethyl]-1,4-dimethylbenzene were as follows.

$^1$H NMR (DMSO-d$_6$): δ 8.40 (s, 1H), 7.24 (s, 1H), 7.15 (s, 2H), 2.49 (s, 3H), 2.26 (s, 3H).
$^{19}$F NMR (DMSO-d$_6$): δ −71.9 (s, 6F, CF$_3$).

A 5 L reactor was charged with 200.0 g (0.676 mol) of the obtained 2-[2,2,2-trifluoro-1-hydroxy-1-(trifluoromethyl)ethyl]-1,4-dimethylbenzene (purity: 92%) and 3.0 L of 0.15N NaOH, followed by heating to 85° C. Then, 480.7 g (3.04 mol/4.5 eq) of potassium permanganate was gradually added by spending 3 hr, followed by stirring at 90° C. for 4 hr. After the reaction, 200 mL of concentrated hydrochloric acid was added, followed by discoloring with sodium sulfite and extraction with 1.4 L of diisopropyl ether. Furthermore, the aqueous layer was extracted two times with 500 mL of diisopropyl ether. The combined organic layer was dehydrated with anhydrous magnesium sulfate, followed by filtration, concentration and drying, thereby obtaining a pale yellow powder. To the obtained pale yellow powder 560 mL of toluene and 80 mL of acetonitrile were added, followed by reflux and cooling to conduct recrystallization, thereby obtaining 131.1 g of the target 2-[2,2,2-trifluoro-1-hydroxy-1-(trifluoromethyl)ethyl]-1,4-benzenedicarboxylic acid represented by the following formula. Upon this, yield was 58%, and purity was 99.8%.

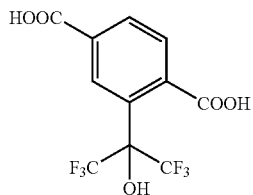

The properties of the obtained 2-[2,2,2-trifluoro-1-hydroxy-1-(trifluoromethyl)ethyl]-1,4-benzenedicarboxylic acid were as follows.

$^1$H NMR (DMSO-d$_6$): δ 8.45 (d, J=7.6 Hz, 1H), 8.31 (d, J=7.6 Hz, 1H), 8.27 (s, 1H).
$^{13}$C NMR (DMSO-d$_6$): δ 165.16 (s), 164.62 (s), 138.93 (s), 136.24 (s), 135.2-134.5 (m), 128.8-127.9 (m), 127.56 (s), 124.9-123.8 (m), 120.48 (q, J=284.7 Hz), 80.89 (sept, J=33.0 Hz).
$^{19}$F NMR (DMSO-d$_6$): δ −73.8 (s, 6F, CF$_3$).

Example 3

Production of 5-[2,2,2-Trifluoro-1-Hydroxy-1-(Trifluoromethyl)Ethyl]-1,3-Benzenedicarboxylic Acid (Dicarboxylic Acid 3)

Under nitrogen atmosphere, a 500 mL glass flask was charged with 30.0 g (95.0 mmol) of 1,3,5-tribromobenzene and 400 mL of diethyl ether, followed by cooling to −78° C. At −78° C., 60 mL of a 1.6M solution containing 96.0 mmol of n-butyllithium in hexane was added dropwise by spending 1 hr, followed by aging at −78° C. for 1 hr. After confirming lithiation by gas chromatography, 16.6 g (100.0 mmol) of hexafluoroacetone was bubbled at −78° C., followed by stirring for 1 hr. After stirring, the reaction liquid was added to 400 mL of 2N hydrochloric acid to separate it into an organic layer and an aqueous layer. The aqueous layer was extracted with 100 mL of isopropyl ether. The combined organic layer was dried with anhydrous magnesium sulfate, followed by concentration with an evaporator and then solid distillation, thereby obtaining 23.0 g of 1-[2,2,2-trifluoro-1-hydroxy-1-(trifluoromethyl)ethyl]-3,5-dibromobenzene (yield: 60%) represented by the following formula.

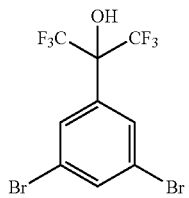

The properties of 1-[2,2,2-trifluoro-1-hydroxy-1-(trifluoromethyl)ethyl]-3,5-dibromobenzene were as follows.

$^1$H NMR (CDCl$_3$): δ 7.79 (S, 3H).
$^{19}$F NMR (CDCl$_3$): δ −76.0 (S, 6F, CF$_3$).

A 10 mL autoclave was charged with 1.00 g (2.6 mmol) of the obtained 1-[2,2,2-trifluoro-1-hydroxy-1-(trifluoromethyl)ethyl]-3,5-dibromobenzene, 0.056 g (0.25 mmol) of palladium acetate, 0.263 g (1.0 mmol) of triphenylphosphine, 1.01 g (10.0 mmol) of triethylamine, 0.50 g of water, and 2.0 g of tetrahydrofuran. Then, the reaction was conducted at 100° C. for 17 hr under a carbon monoxide pressure of 2 MPa. After the reaction, 5 mL of 2N hydrochloric acid was added to the reaction liquid, followed by extraction with 5 mL of isopropyl ether to separate an organic layer. To this organic layer 6 mL of 7% sodium hydroxide aqueous solution was added to separate an aqueous layer. This aqueous layer was washed with 3 mL of heptane, followed by adding 6 mL of 6N hydrochloric acid. The precipitated solid was isolated by filtration and then washed with 5 mL of heptane, thereby obtaining 0.35 g of 5-[2,2,2-trifluoro-1-hydroxy-1-(trifluoromethyl)ethyl]-1,3-benzenedicarboxylic acid (yield: 41%) represented by the following formula.

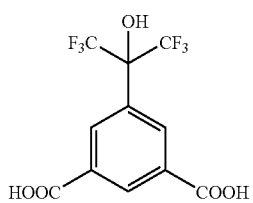

The properties of 5-[2,2,2-trifluoro-1-hydroxy-1-(trifluoromethyl)ethyl]-1,3-benzenedicarboxylic acid were as follows.

$^1$H NMR (CDCl$_3$): δ 9.27 (S, 1H), 8.58 (t, 1H), 8.46 (s, 2H).
$^{19}$F NMR (CDCl$_3$): δ −73.5 (S, 6F, CF$_3$).

Example 4

Synthesis of Polymer 1

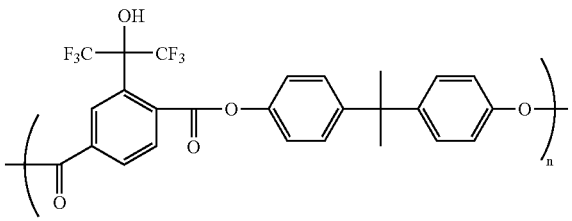

POLYMER 1

A three-necked flask was charged with 2.00 g (6.0 mmol) of Dicarboxylic Acid 2, 1.37 g (6.0 mmol) of bisphenol A, 4.19 g (12.6 mmol) of triphenylphosphine dichloride as a condensing agent, and 12.0 g of N-methyl-2-pyrrolidone (NMP), followed by stirring at room temperature for 3 hr under nitrogen atmosphere. The obtained viscous solution was added to 30 mL of methanol. The obtained precipitate was separated by filtration, followed by vacuum drying at 80° C., thereby obtaining 2.84 g of Polymer 1 (yield: 91%). The result is shown in Table 1.

1.00 g of the obtained Polymer 1 and 4.00 g of N,N-dimethylformamide (DMF) were mixed together to prepare a homogeneous solution. This solution was filtered, and the filtrate was applied onto a glass substrate by spin coating, followed by heating under nitrogen atmosphere at 80° C. for 30 min, at 150° C. for 30 min, and at 250° C. for 1 hr, thereby obtaining a transparent film. After the film was separated from the glass substrate, the film maintained its shape. The properties of the film are shown in Table 2.

Example 5

Synthesis of Polymer 2

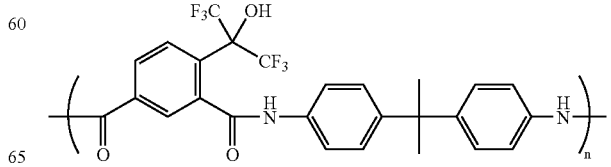

POLYMER 2

A three-necked flask was charged with 2.00 g (6.0 mmol) of Dicarboxylic Acid 1, 1.37 g (6.0 mmol) of Diamine 1 represented by the following formula,

DIAMINE 1

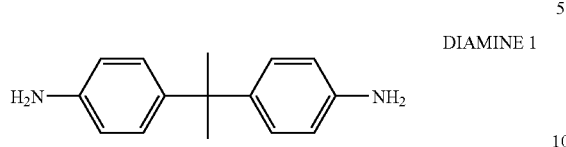

4.19 g (12.6 mmol) of triphenylphosphine dichloride as a condensing agent, and 19.0 g of N-methyl-2-pyrrolidone (NMP), followed by the same steps as those of Example 4, thereby obtaining Polymer 2 (yield: 90%). The result is shown in Table 1.

1.00 g of the obtained Polymer 2 and 4.00 g of N,N-dimethylformamide (DMF) were mixed together to prepare a homogeneous solution. This solution was filtered, and the filtrate was applied onto a glass substrate by spin coating, followed by heating under nitrogen atmosphere at 80° C. for 30 min, at 150° C. for 30 min, and at 250° C. for 1 hr, thereby obtaining a transparent film. After the film was separated from the glass substrate, the film maintained its shape. The properties of the film are shown in Table 2.

Example 6

Synthesis of Polymer 3

POLYMER 3

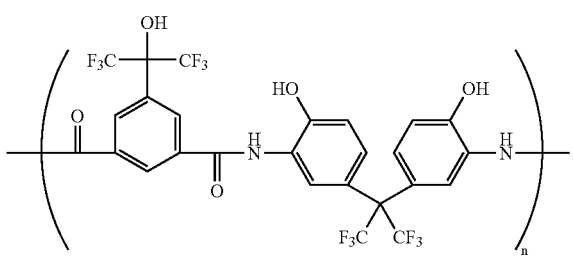

A three-necked flask was charged with 2.00 g (6.0 mmol) of Dicarboxylic Acid 3, 2.20 g (6.0 mmol) of Bisaminophenol 1 represented by the following formula,

BISAMINOPHENOL 1

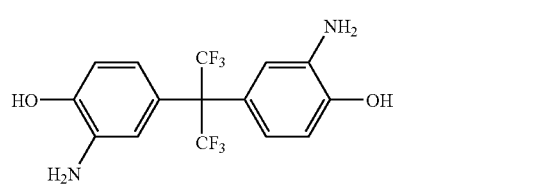

4.19 g (12.6 mmol) of triphenylphosphine dichloride as a condensing agent, and 20.0 g of N-methyl-2-pyrrolidone (NMP), followed by the same steps as those of Example 4, thereby obtaining Polymer 3 (yield: 85%). The result is shown in Table 1.

Example 7

Synthesis of Polymer 4

POLYMER 4

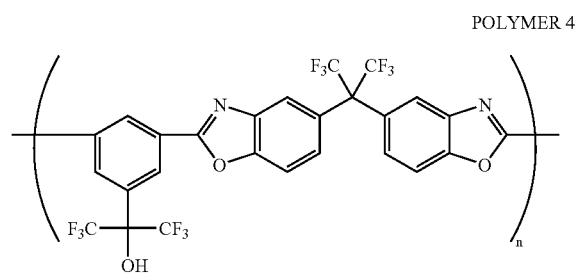

1.00 g of Polymer 3 obtained by Example 3 and 4.00 g of N,N-dimethylformamide (DMF) were mixed together to prepare a homogeneous solution. This solution was filtered, and the filtrate was applied onto a glass substrate by spin coating, followed by heating under nitrogen atmosphere at 80° C. for 30 min, at 150° C. for 30 min, at 250° C. for 30 min, and at 320° C. for 1 hr, thereby obtaining a transparent film. After the film was separated from the glass substrate, the film maintained its shape. The film was found to have a structure of Polymer 4 by IR analysis. The properties of the film are shown in Table 2.

Example 8

Synthesis of Polymer 5

POLYMER 5

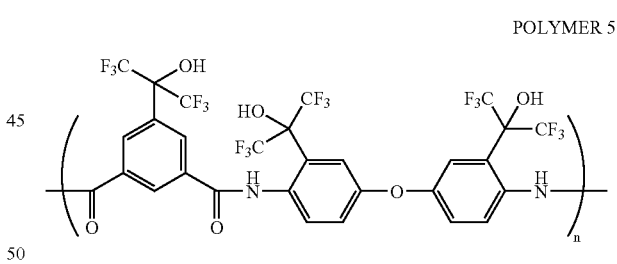

A three-necked flask was charged with 2.00 g (6.0 mmol) of Dicarboxylic Acid 3, 3.19 g (6.0 mmol) of Diaminodiol 1 represented by the following formula,

DIAMINODIOL 1

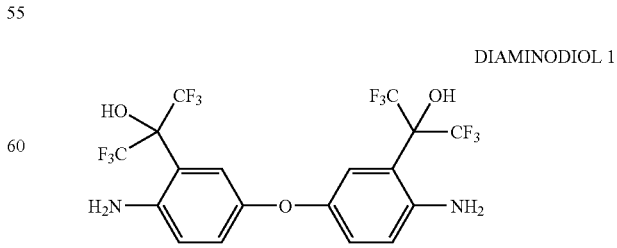

4.19 g (12.6 mmol) of triphenylphosphine dichloride as a condensing agent, and 26.0 g of N-methyl-2-pyrrolidone (NMP), followed by the same steps as those of Example 4, thereby obtaining Polymer 5 (yield: 87%). The result is shown in Table 1.

Example 9

Synthesis of Polymer 6

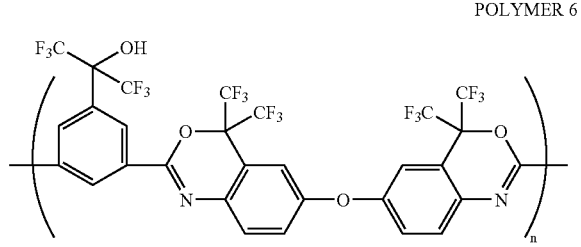

POLYMER 6

1.00 g of Polymer 5 obtained by Example 8 and 4.00 g of DMF were mixed together to prepare a homogeneous solution. This solution was filtered, and the filtrate was applied onto a glass substrate by spin coating, followed by heating under nitrogen atmosphere at 80° C. for 30 min, at 150° C. for 30 min, and at 250° C. for 1 hr, thereby obtaining a transparent film. After the film was separated from the glass substrate, the film maintained its shape. The film was found to have a structure of Polymer 6 by IR analysis. The properties of the film are shown in Table 2.

Comparative Example 1

Synthesis of Polymer 7

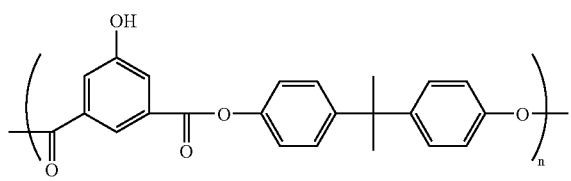

POLYMER 7

Example 4 was repeated except in that Dicarboxylic Acid 2 was replaced with Dicarboxylic Acid 4 represented by the following formula.

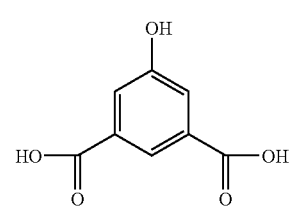

DICARBOXYLIC ACID 4

With this, a transparent film was obtained. After the film was separated from the glass substrate, the film maintained its shape. The properties of the film are shown in Table 2.

Comparative Example 2

Synthesis of Polymer 8

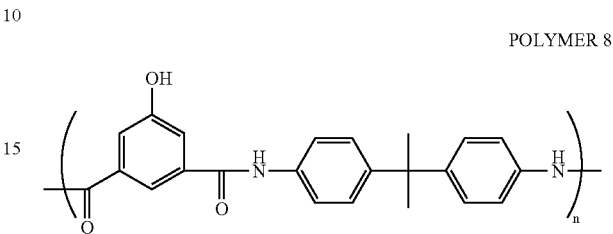

POLYMER 8

Example 5 was repeated except in that Dicarboxylic Acid 1 was replaced with Dicarboxylic Acid 4 of Comparative Example 1. With this, a transparent film was obtained. After the film was separated from the glass substrate, the film maintained its shape. The properties of the film are shown in Table 2.

Comparative Example 3

Synthesis of Polymer 9

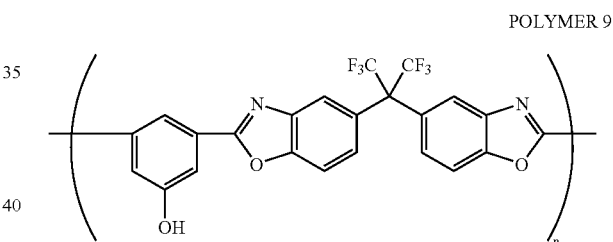

POLYMER 9

Example 6 was repeated except in that Dicarboxylic Acid 3 was replaced with Dicarboxylic Acid 4 of Comparative Example 1. The resulting polymer was subjected to the same procedures as those of Example 7, thereby obtaining a transparent film having a structure of Polymer 9. After the film was separated from the glass substrate, the film maintained its shape. The properties of the film are shown in Table 2.

Comparative Example 4

Synthesis of Polymer 10

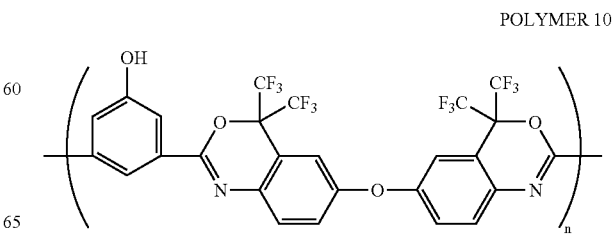

POLYMER 10

Example 8 was repeated except in that Dicarboxylic Acid 3 was replaced with Dicarboxylic Acid 4 of Comparative Example 1. The resulting polymer was subjected to the same procedures as those of Example 9, thereby obtaining a transparent film having a structure of Polymer 10. After the film was separated from the glass substrate, the film maintained its shape. The properties of the film are shown in Table 2.

TABLE 1

|  | Polymer No. | Mw (Mw/Mn) |
|---|---|---|
| Example 4 | 1 | 25,000 (2.34) |
| Example 5 | 2 | 31,000 (2.52) |
| Example 6 | 3 | 37,000 (2.17) |
| Example 8 | 5 | 32,000 (2.45) |

TABLE 2

|  | Polymer No. | Dielectric Constant | Water Absorption (%) |
|---|---|---|---|
| Example 4 | 1 | 3.10 | 2.00 |
| Example 5 | 2 | 3.40 | 3.30 |
| Example 7 | 4 | 2.70 | 2.60 |
| Example 9 | 6 | 2.50 | 2.42 |
| Com. Ex. 1 | 7 | 3.40 | 2.40 |
| Com. Ex. 2 | 8 | 3.60 | 4.00 |
| Com. Ex. 3 | 9 | 3.20 | 3.20 |
| Com. Ex. 4 | 10 | 3.00 | 3.05 |

It is understood from Table 2 that Polymers 1, 2, 4 and 6 according to Examples 4, 5, 7 and 9, each polymer having a hexafluoroisopropanol group, are respectively lower in dielectric constant and water absorption than Polymers 7 to 10 according to Comparative Examples 1 to 4, each polymer having a phenolic hydroxy group, in contrast with the hexafluoroisopropanol group.

The entire contents of Japanese Patent Application No. 2007-185257 (filed Jul. 17, 2007), of which priority is claimed in the present application, are incorporated herein by reference.

What is claimed is:

1. A fluorine-containing dicarboxylic acid represented by formula (1),

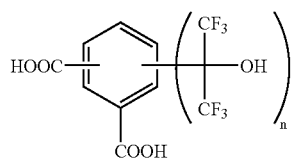

(1)

wherein n represents an integer of 1-4, and the two carboxylic groups are not adjacent to each other on the aromatic ring.

2. A fluorine-containing dicarboxylic acid according to claim 1, which is 5-[2,2,2-trifluoro-1-hydroxy-1-(trifluoromethyl)ethyl]-1,3-benzenedicarboxylic acid.

3. A fluorine-containing dicarboxylic acid according to claim 1, which is 2-[2,2,2-trifluoro-1-hydroxy-1-(trifluoromethyl)ethyl]-1,4-benzenedicarboxylic acid.

4. A fluorine-containing dicarboxylic acid according to claim 1, which is 4-[2,2,2-trifluoro-1-hydroxy-1-(trifluoromethyl)ethyl]-1,3-benzenedicarboxylic acid.

5. A process for producing 5-[2,2,2-trifluoro-1-hydroxy-1-(trifluoromethyl)ethyl]-1,3-benzenedicarboxylic acid, comprising the step of carbonylating 5-[2,2,2-trifluoro-1-hydroxy-1-(trifluoromethyl)ethyl]-1,3-dihalobenzene represented by formula (12),

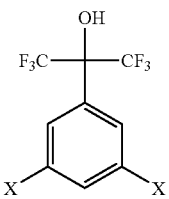

(12)

wherein X represents a halogen that is fluorine, chlorine, bromine or iodine, trifluoromethanesulfonate group, $C_1$-$C_4$ alkylsulfonate group, or arylsulfonate group.

6. A process for producing 5-[2,2,2-trifluoro-1-hydroxy-1-(trifluoromethyl)ethyl]-1,3-benzenedicarboxylic acid, comprising the steps of:

(a) reacting a 1,3,5-trihalobenzene represented by formula (13),

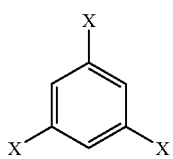

(13)

wherein X represents a halogen that is fluorine, chlorine, bromine or iodine, trifluoromethanesulfonate group, $C_1$-$C_4$ alkylsulfonate group, or arylsulfonate group, with an alkylmagnesium halide, metallic magnesium or alkyllithium;

(b) treating a product of the step (a) with hexafluoroacetone, thereby obtaining 5-[2,2,2-trifluoro-1-hydroxy-1-(trifluoromethyl)ethyl]-1,3-dihalobenzene represented by formula (12),

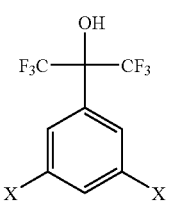

(12)

wherein X is defined, as above, and (c) carbonylating the 5-[2,2,2-trifluoro-1-hydroxy-1-(trifluoromethyl)ethyl]-1,3-dihalobenzene into 5-[2,2,2-trifluoro-1-hydroxy-1-(trifluoromethyl)ethyl]-1,3-benzenedicarboxylic acid.

7. A process according to claim 6, wherein the carbonylation of the step (c) is conducted by reacting 5-[2,2,2-trifluoro-1-hydroxy-1-(trifluoromethyl)ethyl]-1,3-dihalobenzene with carbon monoxide in the presence of a palladium catalyst and a basic substance.

8. A process according to claim 6, wherein the carbonylation of the step (c) is conducted by the steps of:

(d) reacting 5-[2,2,2-trifluoro-1-hydroxy-1-(trifluoromethyl)ethyl]-1,3-dihalobenzene with an alkylmagnesium halide, metallic magnesium, or alkyllithium, and (e) reacting a product of the step (d) with carbon dioxide.

* * * * *